US012589006B2

(12) United States Patent (10) Patent No.: US 12,589,006 B2

Harper et al. (45) Date of Patent: Mar. 31, 2026

(54) EXPANDABLE VERTEBRAL IMPLANT AND METHOD

(71) Applicant: SeaSpine Orthopedics Corporation, Carlsbad, CA (US)

(72) Inventors: Michael Roscoe Harper, Carlsbad, CA (US); Samuel Hunter Hatcher, Carlsbad, CA (US); Adam James Lipson, San Marcos, CA (US)

(73) Assignee: SeaSpine Orthopedics Corporation, Carlsbad, CA (US)

( * ) Notice: Subject to any disclaimer, the term of this patent is extended or adjusted under 35 U.S.C. 154(b) by 0 days.

(21) Appl. No.: 17/938,152

(22) Filed: Oct. 5, 2022

(65) Prior Publication Data

US 2023/0115853 A1 Apr. 13, 2023

Related U.S. Application Data

(60) Provisional application No. 63/253,784, filed on Oct. 8, 2021.

(51) Int. Cl.
*A61F 2/44* (2006.01)

(52) U.S. Cl.
CPC ................................. *A61F 2/4465* (2013.01)

(58) Field of Classification Search
CPC .................. A61F 2250/0004–2250/001; A61F 2250/0048; A61F 2220/0025–0091; A61F 2002/30329–30528; A61F 2/44; A61F 2002/4627; A61F 2/4465; A61F 2/4455–2/447

See application file for complete search history.

(56) References Cited

U.S. PATENT DOCUMENTS

| 1,036,204 | A | 8/1912 | Farnham |
| 1,457,825 | A | 6/1923 | Devan |
| 1,512,842 | A | 10/1924 | Givens |
| 2,620,001 | A | 12/1952 | Fratz |

(Continued)

FOREIGN PATENT DOCUMENTS

| CA | 2088066 A1 | 1/1992 |
| CA | 2015507 C | 1/1999 |

(Continued)

OTHER PUBLICATIONS

European Patent Office; International Search Report and Written Opinion issued for Application No. PCT/US2022/077611, 7 pages, dated Feb. 2, 2023.

(Continued)

*Primary Examiner* — Eduardo C Robert
*Assistant Examiner* — Michelle C Green
(74) *Attorney, Agent, or Firm* — Dinsmore & Shohl LLP

(57) ABSTRACT

A system and methods for assembling an expandable vertebral implant for engagement between vertebrae. The implant may expand and/or collapse between a variety of lengths. The implant may include an inner core, an outer core, and/or a middle core such that the inner and outer cores may be moveable relative to each other along an axis. The middle core may include one or more gear teeth. The implant may include one or more locking mechanisms. The implant may include one or more endplates. One endplate may be fixed and/or polyaxial. A tool may be used to vary the length of the implant.

42 Claims, 32 Drawing Sheets

(56) References Cited

U.S. PATENT DOCUMENTS

| | | |
|---|---|---|
| 2,677,369 A | 5/1954 | Knowles |
| 3,307,505 A | 3/1967 | Windross |
| 3,745,995 A | 7/1973 | Kraus |
| 3,774,244 A | 11/1973 | Walker |
| 3,837,753 A | 9/1974 | Weiste |
| 3,848,601 A | 11/1974 | Ma |
| 3,855,638 A | 12/1974 | Pilliar |
| 3,867,728 A | 2/1975 | Stubstad |
| 3,894,467 A | 7/1975 | Brescia |
| 3,906,550 A | 9/1975 | Rostoker |
| 4,011,602 A | 3/1977 | Rybicki |
| 4,026,304 A | 5/1977 | Levy |
| 4,126,057 A | 11/1978 | Von Allworden |
| 4,203,430 A | 5/1980 | Takahashi |
| 4,285,071 A | 8/1981 | Nelson |
| 4,309,777 A | 1/1982 | Patil |
| 4,349,921 A | 9/1982 | Kuntz |
| 4,429,691 A | 2/1984 | Niwa |
| 4,484,570 A | 11/1984 | Sutter |
| 4,501,269 A | 2/1985 | Bagby |
| 4,542,539 A | 9/1985 | Rowe, Jr. |
| 4,553,273 A | 11/1985 | Wu |
| 4,554,914 A | 11/1985 | Kapp |
| 4,563,778 A | 1/1986 | Roche |
| 4,611,582 A | 9/1986 | Duff |
| 4,657,550 A | 4/1987 | Daher |
| 4,693,721 A | 9/1987 | Ducheyne |
| 4,714,469 A | 12/1987 | Kenna |
| 4,736,738 A | 4/1988 | Lipovsek |
| 4,743,256 A | 5/1988 | Brantigan |
| 4,759,766 A | 7/1988 | Buettner-Janz |
| 4,781,591 A | 11/1988 | Allen |
| 4,820,305 A | 4/1989 | Harms |
| 4,834,757 A | 5/1989 | Brantigan |
| 4,877,020 A | 10/1989 | Vich |
| 4,878,915 A | 11/1989 | Brantigan |
| 4,892,546 A | 1/1990 | Kotz |
| 4,932,975 A | 6/1990 | Main |
| 4,938,768 A | 7/1990 | Wu |
| 4,946,378 A | 8/1990 | Hirayama |
| 4,961,740 A | 10/1990 | Ray |
| 5,026,373 A | 6/1991 | Ray |
| 5,055,104 A | 10/1991 | Ray |
| 5,059,193 A | 10/1991 | Kuslich |
| 5,062,845 A | 11/1991 | Kuslich |
| 5,071,437 A | 12/1991 | Steffee |
| 5,133,717 A | 7/1992 | Chopin |
| 5,147,402 A | 9/1992 | Bohler |
| 5,171,278 A | 12/1992 | Pisharodi |
| 5,171,281 A | 12/1992 | Parsons |
| 5,192,326 A | 3/1993 | Bao |
| 5,192,327 A | 3/1993 | Brantigan |
| 5,201,766 A | 4/1993 | Georgette |
| 5,222,983 A | 6/1993 | Schmitz |
| 5,236,460 A | 8/1993 | Barber |
| 5,250,061 A | 10/1993 | Michelson |
| 5,290,312 A | 3/1994 | Kojimoto |
| 5,290,494 A | 3/1994 | Coombes |
| 5,300,076 A | 4/1994 | Leriche |
| 5,304,210 A | 4/1994 | Crook |
| 5,306,307 A | 4/1994 | Senter |
| 5,306,309 A | 4/1994 | Wagner |
| 5,312,405 A | 5/1994 | Moser |
| 5,314,478 A | 5/1994 | Oka |
| 5,330,535 A | 7/1994 | Moser |
| 5,336,223 A | 8/1994 | Rogers |
| 5,364,400 A | 11/1994 | Rego, Jr. |
| 5,390,683 A | 2/1995 | Pisharodi |
| 5,395,372 A | 3/1995 | Holt |
| 5,397,364 A | 3/1995 | Kozak |
| 5,405,391 A | 4/1995 | Henderson |
| 5,413,602 A | 5/1995 | Metz-Stavenhagen |
| 5,423,818 A | 6/1995 | Van Hoeck et al. |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen |
| 5,445,639 A | 8/1995 | Kuslich |
| 5,454,811 A | 10/1995 | Huebner |
| 5,458,638 A | 10/1995 | Kuslich |
| 5,458,641 A | 10/1995 | Ramirez Jimenez |
| 5,458,643 A | 10/1995 | Oka |
| 5,489,308 A | 2/1996 | Kuslich |
| 5,514,180 A | 5/1996 | Heggeness |
| 5,522,879 A | 6/1996 | Scopelianos |
| 5,522,899 A | 6/1996 | Michelson |
| 5,524,624 A | 6/1996 | Tepper |
| 5,534,030 A | 7/1996 | Navarro |
| 5,545,229 A | 8/1996 | Parsons |
| 5,549,679 A | 8/1996 | Kuslich |
| 5,562,736 A | 10/1996 | Ray |
| 5,562,738 A | 10/1996 | Boyd |
| 5,565,005 A | 10/1996 | Erickson |
| 5,571,190 A | 11/1996 | Ulrich |
| 5,571,192 A | 11/1996 | Schonhoffer |
| 5,582,612 A | 12/1996 | Lin |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs |
| 5,609,637 A | 3/1997 | Biedermann |
| 5,645,598 A | 7/1997 | Brosnahan, III |
| 5,653,761 A | 8/1997 | Pisharodi |
| 5,653,762 A | 8/1997 | Pisharodi |
| 5,653,763 A | 8/1997 | Errico et al. |
| 5,658,336 A | 8/1997 | Pisharodi |
| 5,658,337 A | 8/1997 | Kohrs |
| 5,664,762 A | 9/1997 | Rothbauer |
| 5,665,089 A | 9/1997 | Dall |
| 5,665,119 A | 9/1997 | Koller |
| 5,665,122 A | 9/1997 | Kambin |
| 5,667,506 A | 9/1997 | Sutterlin |
| 5,669,909 A | 9/1997 | Zdeblick |
| 5,669,910 A | 9/1997 | Korhonen |
| 5,674,294 A | 10/1997 | Bainville |
| 5,683,393 A | 11/1997 | Ralph |
| 5,683,394 A | 11/1997 | Rinner |
| 5,683,464 A | 11/1997 | Wagner |
| 5,700,264 A | 12/1997 | Zucherman |
| 5,700,291 A | 12/1997 | Kuslich |
| 5,702,449 A | 12/1997 | Mckay |
| 5,702,451 A | 12/1997 | Biedermann |
| 5,702,453 A | 12/1997 | Rabbe |
| 5,702,455 A * | 12/1997 | Saggar ..................... A61F 2/44 |
| | | 623/17.15 |
| 5,707,372 A | 1/1998 | Errico et al. |
| 5,711,957 A | 1/1998 | Patat |
| 5,716,415 A | 2/1998 | Steffee |
| 5,723,013 A | 3/1998 | Jeanson |
| 5,749,916 A | 5/1998 | Richelsoph |
| 5,766,176 A | 6/1998 | Duncan |
| 5,766,252 A | 6/1998 | Henry |
| 5,766,253 A | 6/1998 | Brosnahan, III |
| 5,772,661 A | 6/1998 | Michelson |
| 5,776,197 A | 7/1998 | Hiromi |
| 5,776,198 A | 7/1998 | Rabbe |
| 5,776,199 A | 7/1998 | Michelson |
| 5,782,830 A | 7/1998 | Farris |
| 5,782,832 A | 7/1998 | Larsen |
| 5,782,919 A | 7/1998 | Zdeblick |
| 5,785,710 A | 7/1998 | Michelson |
| 5,797,909 A | 8/1998 | Michelson |
| 5,800,547 A | 9/1998 | Bernd |
| 5,800,549 A | 9/1998 | Bao |
| 5,800,550 A | 9/1998 | Sertich |
| 5,814,048 A | 9/1998 | Morgan |
| 5,814,084 A | 9/1998 | Grivas |
| D403,069 S | 12/1998 | Drewry |
| 5,865,845 A | 2/1999 | Thalgott |
| 5,865,848 A | 2/1999 | Baker |
| 5,885,299 A | 3/1999 | Winslow |
| 5,888,222 A | 3/1999 | Coates |
| 5,888,224 A | 3/1999 | Beckers |
| 5,888,227 A | 3/1999 | Cottle |

(56) References Cited

U.S. PATENT DOCUMENTS

| | | | |
|---|---|---|---|
| 5,893,889 A | 4/1999 | Harrington |
| 5,893,890 A | 4/1999 | Pisharodi |
| 5,897,085 A | 4/1999 | Cronin |
| 5,897,556 A | 4/1999 | Drewry |
| 5,904,719 A | 5/1999 | Errico |
| 5,910,315 A | 6/1999 | Stevenson |
| 5,913,860 A | 6/1999 | Scholl |
| 5,947,966 A | 9/1999 | Drewry |
| 5,951,556 A | 9/1999 | Faccioli |
| 5,957,836 A | 9/1999 | Johnson |
| 5,961,554 A | 10/1999 | Janson |
| 5,968,062 A | 10/1999 | Thomas |
| 5,968,098 A | 10/1999 | Winslow |
| 5,972,031 A | 10/1999 | Biedermann |
| 5,980,523 A | 11/1999 | Jackson |
| 5,980,540 A | 11/1999 | Bruce |
| 5,989,289 A | 11/1999 | Coates |
| 5,989,290 A | 11/1999 | Biedermann |
| 6,004,326 A | 12/1999 | Castro |
| 6,015,436 A | 1/2000 | Helmut |
| 6,015,439 A | 1/2000 | Pedemonte |
| 6,019,793 A | 2/2000 | Perren |
| 6,033,405 A | 3/2000 | Winslow |
| 6,039,762 A | 3/2000 | Mckay |
| 6,045,579 A | 4/2000 | Hochschuler |
| 6,059,829 A | 5/2000 | Fridolin |
| 6,063,088 A | 5/2000 | Fridolin |
| 6,066,175 A | 5/2000 | Henderson |
| 6,074,423 A | 6/2000 | Lawson |
| 6,080,155 A | 6/2000 | Michelson |
| 6,080,193 A | 6/2000 | Hochschuler |
| 6,083,225 A | 7/2000 | Winslow |
| 6,090,143 A | 7/2000 | Meriwether |
| 6,093,205 A | 7/2000 | Mcleod |
| 6,093,207 A | 7/2000 | Pisharodi |
| 6,096,038 A | 8/2000 | Michelson |
| 6,099,483 A | 8/2000 | Palmer |
| 6,102,948 A | 8/2000 | Brosnahan, III |
| 6,102,950 A | 8/2000 | Vaccaro |
| 6,106,557 A | 8/2000 | Robioneck |
| 6,113,600 A | 9/2000 | Drummond et al. |
| 6,113,638 A | 9/2000 | Williams |
| 6,120,503 A | 9/2000 | Michelson |
| 6,120,506 A | 9/2000 | Kohrs |
| 6,123,705 A | 9/2000 | Michelson |
| 6,126,660 A | 10/2000 | Dietz |
| 6,126,689 A | 10/2000 | Brett |
| 6,136,031 A | 10/2000 | Middleton |
| 6,143,032 A | 11/2000 | Schafer |
| 6,143,033 A | 11/2000 | Paul |
| 6,149,651 A | 11/2000 | Drewry |
| 6,159,211 A | 12/2000 | Boriani |
| 6,159,244 A | 12/2000 | Suddaby |
| 6,174,311 B1 | 1/2001 | Branch |
| 6,174,334 B1 | 1/2001 | Suddaby |
| 6,176,881 B1 | 1/2001 | Manuel |
| 6,186,613 B1 | 2/2001 | Watanabe |
| 6,190,413 B1 | 2/2001 | Sutcliffe |
| 6,190,414 B1 | 2/2001 | Young et al. |
| 6,193,755 B1 | 2/2001 | Metz-Stavenhagen |
| 6,193,756 B1 | 2/2001 | Studer |
| 6,200,348 B1 | 3/2001 | Biedermann |
| 6,206,924 B1 | 3/2001 | Timm |
| 6,224,595 B1 | 5/2001 | Michelson |
| 6,234,705 B1 | 5/2001 | Troxell |
| 6,238,396 B1 | 5/2001 | Lombardo |
| 6,238,397 B1 | 5/2001 | Zucherman |
| 6,241,729 B1 | 6/2001 | Estes |
| 6,245,072 B1 | 6/2001 | Zdeblick |
| 6,245,108 B1 | 6/2001 | Biscup |
| 6,248,104 B1 | 6/2001 | Chopin |
| 6,258,125 B1 | 7/2001 | Paul |
| 6,283,967 B1 | 9/2001 | Troxell |
| 6,290,724 B1 | 9/2001 | Marino |
| 6,296,665 B1 | 10/2001 | Strnad |
| 6,302,882 B1 | 10/2001 | Lin |
| 6,306,137 B2 | 10/2001 | Troxell |
| D450,121 S | 11/2001 | Anderson |
| 6,315,797 B1 | 11/2001 | Middleton |
| 6,325,827 B1 | 12/2001 | Lin |
| 6,328,741 B1 | 12/2001 | Richelsoph |
| 6,332,895 B1 | 12/2001 | Suddaby |
| 6,344,057 B1 | 2/2002 | Rabbe |
| 6,371,988 B1 | 4/2002 | Pafford |
| 6,375,681 B1 | 4/2002 | Truscott |
| 6,375,683 B1 | 4/2002 | Crozet et al. |
| 6,395,034 B1 | 5/2002 | Suddaby |
| 6,395,035 B2 | 5/2002 | Bresina |
| 6,402,751 B1 | 6/2002 | Hoeck |
| 6,409,765 B1 | 6/2002 | Bianchi |
| 6,409,766 B1 | 6/2002 | Brett |
| 6,413,258 B1 | 7/2002 | Bernhardt, Jr. |
| 6,419,705 B1 | 7/2002 | Erickson |
| 6,425,920 B1 | 7/2002 | Hamada |
| 6,428,544 B1 | 8/2002 | Ralph |
| 6,435,048 B2 | 8/2002 | Zimmerman |
| 6,436,101 B1 | 8/2002 | Hamada |
| 6,440,142 B1 | 8/2002 | Ralph |
| 6,443,987 B1 | 9/2002 | Bryan |
| 6,454,805 B1 | 9/2002 | Baccelli |
| 6,454,806 B1 | 9/2002 | Cohen |
| 6,458,159 B1 | 10/2002 | Thalgott |
| 6,468,311 B2 | 10/2002 | Boyd |
| 6,471,724 B2 | 10/2002 | Zdeblick |
| 6,471,958 B2 | 10/2002 | Dimitrijevich |
| 6,478,801 B1 | 11/2002 | Ralph |
| 6,478,823 B1 | 11/2002 | Michelson |
| 6,494,883 B1 | 12/2002 | Ferree |
| 6,500,205 B1 | 12/2002 | Michelson |
| 6,500,206 B1 | 12/2002 | Bryan |
| 6,520,192 B1 | 2/2003 | Lo |
| 6,520,996 B1 | 2/2003 | Manasas |
| 6,524,318 B1 | 2/2003 | Longhini |
| 6,524,341 B2 | 2/2003 | Bruno |
| 6,537,320 B1 | 3/2003 | Michelson |
| 6,544,265 B2 | 4/2003 | Lieberman |
| 6,554,832 B2 | 4/2003 | Shluzas |
| 6,562,074 B2 | 5/2003 | Gerbec |
| 6,565,574 B2 | 5/2003 | Michelson |
| 6,575,981 B1 | 6/2003 | Boyd |
| 6,578,240 B2 | 6/2003 | Fortenberry |
| 6,582,432 B1 | 6/2003 | Michelson |
| 6,582,437 B2 | 6/2003 | Dorchak |
| 6,585,749 B2 | 7/2003 | Hanson |
| 6,585,770 B1 | 7/2003 | White |
| 6,595,995 B2 | 7/2003 | Zdeblick |
| 6,602,253 B2 | 8/2003 | Richelsoph |
| 6,607,557 B1 | 8/2003 | Brosnahan |
| 6,613,091 B1 | 9/2003 | Zdeblick |
| 6,616,668 B2 | 9/2003 | Altarac |
| 6,616,671 B2 | 9/2003 | Landry |
| 6,616,695 B1 | 9/2003 | Crozet |
| 6,645,206 B1 | 11/2003 | Zdeblick |
| 6,648,894 B2 | 11/2003 | Abdelgany |
| 6,648,895 B2 | 11/2003 | Burkus |
| 6,648,915 B2 | 11/2003 | Sazy |
| 6,648,917 B2 | 11/2003 | Gerbec |
| 6,652,533 B2 | 11/2003 | O'Neil |
| 6,652,584 B2 | 11/2003 | Michelson |
| 6,660,038 B2 | 12/2003 | Boyer, II |
| 6,666,866 B2 | 12/2003 | Martz |
| 6,676,703 B2 | 1/2004 | Biscup |
| 6,679,887 B2 | 1/2004 | Nicholson |
| 6,682,534 B2 | 1/2004 | Patel |
| 6,692,495 B1 | 2/2004 | Zacouto |
| 6,699,288 B2 | 3/2004 | Moret |
| 6,706,069 B2 | 3/2004 | Berger |
| 6,709,458 B2 | 3/2004 | Michelson |
| 6,712,819 B2 | 3/2004 | Zucherman |
| 6,712,852 B1 | 3/2004 | Chung |
| 6,716,247 B2 | 4/2004 | Michelson |
| 6,719,760 B2 | 4/2004 | Dorchak |
| 6,719,794 B2 | 4/2004 | Gerber |
| 6,719,796 B2 | 4/2004 | Cohen et al. |

(56)                References Cited

U.S. PATENT DOCUMENTS

| | | | |
|---|---|---|---|
| 6,723,096 B1 | 4/2004 | Dorchak |
| 6,723,126 B1 | 4/2004 | Berry |
| 6,726,722 B2 | 4/2004 | Walkenhorst |
| 6,730,068 B2 | 5/2004 | Kashiwagi |
| 6,730,088 B2 | 5/2004 | Yeh |
| 6,730,127 B2 | 5/2004 | Michelson |
| 6,733,533 B1 | 5/2004 | Lozier |
| 6,733,534 B2 | 5/2004 | Sherman |
| 6,733,535 B2 | 5/2004 | Michelson |
| 6,740,091 B2 | 5/2004 | Kohrs |
| 6,743,232 B2 | 6/2004 | Overaker |
| 6,743,234 B2 | 6/2004 | Burkus |
| 6,746,454 B2 | 6/2004 | Winterbottom |
| 6,749,636 B2 | 6/2004 | Michelson |
| 6,752,832 B2 | 6/2004 | Neumann |
| 6,755,841 B2 | 6/2004 | Neumann |
| 6,758,849 B1 | 7/2004 | Michelson |
| 6,758,862 B2 | 7/2004 | Berry |
| 6,761,723 B2 | 7/2004 | Buttermann |
| 6,764,491 B2 | 7/2004 | Frey |
| 6,764,514 B1 | 7/2004 | Li |
| 6,776,798 B2 | 8/2004 | Camino |
| 6,783,547 B2 | 8/2004 | Castro |
| 6,786,890 B2 | 9/2004 | Preuthun et al. |
| RE38,614 E | 10/2004 | Paul |
| 6,802,867 B2 | 10/2004 | Manasas |
| 6,805,715 B2 | 10/2004 | Reuter |
| 6,808,538 B2 | 10/2004 | Paponneau |
| 6,808,638 B1 | 10/2004 | Purdum |
| 6,824,565 B2 | 11/2004 | Muhanna |
| 6,840,941 B2 | 1/2005 | Rogers |
| 6,843,804 B2 | 1/2005 | Bryan |
| 6,852,129 B2 | 2/2005 | Gerbec |
| 6,855,166 B2 | 2/2005 | Kohrs |
| 6,855,167 B2 | 2/2005 | Shimp |
| 6,855,168 B2 | 2/2005 | Crozet |
| 6,863,673 B2 | 3/2005 | Gerbec |
| 6,863,689 B2 | 3/2005 | Ralph |
| 6,866,682 B1 | 3/2005 | An |
| 6,872,208 B1 | 3/2005 | Mcbride et al. |
| 6,890,334 B2 | 5/2005 | Brace et al. |
| 6,890,355 B2 | 5/2005 | Michelson |
| 6,899,734 B2 | 5/2005 | Castro |
| 6,902,566 B2 | 6/2005 | Zucherman |
| 6,902,579 B2 | 6/2005 | Harms |
| 6,908,485 B2 | 6/2005 | Crozet |
| 6,923,810 B1 | 8/2005 | Michelson |
| 6,923,814 B1 | 8/2005 | Hildebrand |
| 6,923,830 B2 | 8/2005 | Michelson |
| 6,929,662 B1 | 8/2005 | Messerli |
| 6,953,477 B2 | 10/2005 | Berry |
| 6,981,975 B2 | 1/2006 | Michelson |
| 6,991,653 B2 | 1/2006 | White |
| 6,991,654 B2 | 1/2006 | Foley |
| 6,997,953 B2 | 2/2006 | Chung |
| 7,001,385 B2 | 2/2006 | Bonutti |
| 7,014,659 B2 | 3/2006 | Boyer, II |
| 7,018,415 B1 | 3/2006 | Mckay |
| 7,022,138 B2 | 4/2006 | Mashburn |
| 7,044,972 B2 | 5/2006 | Mathys, Jr. |
| 7,056,343 B2 | 6/2006 | Bernd |
| 7,063,725 B2 | 6/2006 | Foley |
| 7,077,864 B2 | 7/2006 | Byrd, III |
| 7,087,083 B2 | 8/2006 | Pasquet |
| 7,094,257 B2 | 8/2006 | Mujwid et al. |
| 7,128,762 B2 | 10/2006 | Middleton |
| 7,131,995 B2 | 11/2006 | Biedermann |
| 7,135,025 B2 | 11/2006 | Pohjonen |
| 7,135,042 B2 | 11/2006 | Stoll |
| 7,135,043 B2 | 11/2006 | Nakahara |
| 7,137,997 B2 | 11/2006 | Paul |
| 7,141,068 B2 | 11/2006 | Ross |
| 7,141,070 B2 | 11/2006 | Ralph |
| 7,144,426 B2 | 12/2006 | Ralph |
| 7,147,641 B2 | 12/2006 | Chen |
| 7,147,643 B2 | 12/2006 | Robioneck |
| 7,153,304 B2 | 12/2006 | Robie |
| 7,153,325 B2 | 12/2006 | Kim |
| 7,156,858 B2 | 1/2007 | Schuldt-Hempe |
| 7,156,874 B2 | 1/2007 | Paponneau et al. |
| 7,156,876 B2 | 1/2007 | Moumene |
| 7,160,303 B2 | 1/2007 | Keller |
| 7,163,560 B2 | 1/2007 | Mason |
| 7,166,110 B2 | 1/2007 | Yundt |
| 7,166,129 B2 | 1/2007 | Michelson |
| 7,166,130 B2 | 1/2007 | Ferree |
| 7,166,131 B2 | 1/2007 | Studer |
| 7,169,181 B2 | 1/2007 | Kuras |
| 7,169,182 B2 | 1/2007 | Errico |
| 7,169,183 B2 | 1/2007 | Liu |
| 7,172,595 B1 | 2/2007 | Goble |
| 7,172,628 B2 | 2/2007 | Lamprich |
| 7,179,295 B2 | 2/2007 | Kovacevic |
| 7,179,299 B2 | 2/2007 | Edwards |
| 7,182,781 B1 | 2/2007 | Bianchi |
| 7,182,783 B2 | 2/2007 | Trieu |
| 7,182,784 B2 | 2/2007 | Evans |
| 7,189,242 B2 | 3/2007 | Boyd |
| 7,192,446 B2 | 3/2007 | Shapiro |
| 7,192,447 B2 | 3/2007 | Rhoda |
| 7,195,643 B2 | 3/2007 | Jackson |
| 7,384,431 B2 | 6/2008 | Berry |
| 7,392,151 B2 | 6/2008 | Hannu |
| 7,458,988 B2 | 12/2008 | Trieu |
| 7,544,208 B1 | 6/2009 | Mueller |
| 7,575,601 B2 | 8/2009 | Dickson |
| 7,648,529 B2 | 1/2010 | An |
| 7,674,296 B2 | 3/2010 | Rhoda et al. |
| 7,758,648 B2 | 7/2010 | Castleman |
| 7,811,327 B2 | 10/2010 | Hansell et al. |
| 7,824,445 B2 | 11/2010 | Biro |
| 7,879,096 B2 | 2/2011 | Dickson |
| 7,914,581 B2 | 3/2011 | Dickson |
| 7,981,157 B2 | 7/2011 | Castleman |
| 8,062,366 B2 | 11/2011 | Melkent |
| 8,152,851 B2 | 4/2012 | Mueller |
| 8,152,852 B2 | 4/2012 | Biyani |
| 8,182,537 B2 | 5/2012 | Refai |
| 8,187,331 B2 | 5/2012 | Strohkirch, Jr. et al. |
| 8,197,546 B2 | 6/2012 | Doubler |
| 8,202,321 B2 | 6/2012 | Gerner |
| 8,231,681 B2 | 7/2012 | Castleman |
| 8,241,294 B2 | 8/2012 | Sommerich |
| 8,241,363 B2 | 8/2012 | Sommerich |
| 8,252,054 B2 | 8/2012 | Greenhalgh |
| 8,268,004 B2 | 9/2012 | Castleman |
| 8,273,126 B2 | 9/2012 | Lindner |
| 8,282,683 B2 | 10/2012 | Mclaughlin |
| 8,292,963 B2 | 10/2012 | Miller |
| 8,308,802 B2 | 11/2012 | Rhoda et al. |
| 8,328,871 B2 | 12/2012 | Capote |
| 8,337,558 B2 | 12/2012 | Lindner |
| 8,337,559 B2 | 12/2012 | Hansell et al. |
| 8,353,961 B2 | 1/2013 | Mcclintock |
| 8,366,779 B2 | 2/2013 | Dickson |
| 8,377,140 B2 | 2/2013 | Defalco |
| 8,425,608 B2 | 4/2013 | Dewey |
| 8,425,611 B2 | 4/2013 | Dewey et al. |
| 8,540,770 B2 * | 9/2013 | Woodburn, Sr. .......... A61F 2/44 623/17.11 |
| 8,591,585 B2 | 11/2013 | Mclaughlin |
| 8,591,587 B2 | 11/2013 | Refai |
| 8,597,354 B2 | 12/2013 | Winkler |
| 8,632,592 B2 | 1/2014 | Barrall |
| 8,663,330 B2 | 3/2014 | Mcclintock |
| 8,668,740 B2 | 3/2014 | Rhoda et al. |
| 8,690,950 B2 | 4/2014 | Refai |
| 8,721,723 B2 | 5/2014 | Hansell |
| 8,870,880 B2 | 10/2014 | Himmelberger |
| 8,876,905 B2 | 11/2014 | Frasier |
| 8,882,840 B2 | 11/2014 | Mcclintock |
| 8,992,617 B2 | 3/2015 | Woodburn |
| 9,023,108 B2 | 5/2015 | Hansell et al. |
| 9,034,039 B2 | 5/2015 | Richter |

(56) References Cited

U.S. PATENT DOCUMENTS

| | | | |
|---|---|---|---|
| 9,034,046 | B2 | 5/2015 | Refai |
| 9,050,195 | B2 | 6/2015 | Defalco |
| 9,119,725 | B2 | 9/2015 | Barrall |
| 9,138,324 | B2 | 9/2015 | Prevost |
| 9,144,503 | B2 | 9/2015 | Stinchfield |
| 9,173,747 | B2 | 11/2015 | Hansell |
| 9,180,018 | B2 | 11/2015 | Hansell |
| 9,192,481 | B2 | 11/2015 | Rhoda et al. |
| 9,211,197 | B2 | 12/2015 | Baynham |
| 9,271,842 | B2 | 3/2016 | Davenport |
| 9,271,844 | B2 | 3/2016 | Prevost |
| 9,283,086 | B2 | 3/2016 | Hirschl |
| 9,345,588 | B2 | 5/2016 | Himmelberger |
| 9,358,120 | B2 | 6/2016 | Richter |
| 9,387,090 | B2 | 7/2016 | Arnold |
| 9,393,128 | B2 | 7/2016 | Hansell et al. |
| 9,427,325 | B2 | 8/2016 | Stinchfield |
| 9,474,621 | B2 | 10/2016 | Mclaughlin |
| 9,480,575 | B2 | 11/2016 | Prevost |
| 9,561,113 | B2 | 2/2017 | Howard |
| 9,579,211 | B2 | 2/2017 | Mclaughlin |
| 9,610,169 | B2 | 4/2017 | Howard |
| 9,636,231 | B2 | 5/2017 | Rhoda et al. |
| 9,636,233 | B2 | 5/2017 | Arnold |
| 9,655,738 | B2 | 5/2017 | Stinchfield |
| 9,681,961 | B2 | 6/2017 | Prevost |
| 9,687,357 | B2 | 6/2017 | Bannigan |
| 9,707,091 | B2 | 7/2017 | Mclaughlin |
| 9,707,096 | B2 | 7/2017 | Sutterlin, III |
| 9,724,208 | B2 | 8/2017 | Robinson |
| 9,757,250 | B2 | 9/2017 | Josse |
| 9,782,267 | B2 | 10/2017 | Barrall |
| 9,801,730 | B2 | 10/2017 | Howard |
| 9,808,349 | B2 | 11/2017 | Mclaughlin |
| 9,844,441 | B2 | 12/2017 | Prevost |
| 9,844,446 | B2 | 12/2017 | Mclaughlin |
| 9,877,840 | B2 | 1/2018 | Woodburn, Sr. |
| 9,883,952 | B2 | 2/2018 | Josse |
| 9,889,015 | B2 | 2/2018 | Richter |
| 9,913,735 | B2 | 3/2018 | Himmelberger |
| 9,925,061 | B2 | 3/2018 | Baynham |
| 9,956,090 | B2 | 5/2018 | Baynham |
| 9,962,268 | B2 | 5/2018 | Hansell |
| 9,974,659 | B2 | 5/2018 | Rhoda et al. |
| 9,974,663 | B2 | 5/2018 | Stinchfield |
| 10,004,604 | B2 | 6/2018 | Hirschl |
| 10,004,606 | B2 | 6/2018 | Hirschl |
| 10,143,566 | B2 | 12/2018 | Hyder |
| 10,159,581 | B2 | 12/2018 | Mclaughlin |
| 10,201,432 | B2 | 2/2019 | Refai |
| 10,226,352 | B2 | 3/2019 | Lorenz |
| 10,292,832 | B2 | 5/2019 | Sutterlin, III |
| 10,292,836 | B2 | 5/2019 | Josse |
| 10,314,717 | B2 | 6/2019 | Hansell |
| 10,327,908 | B2 | 6/2019 | Wallenstein |
| 10,369,000 | B2 | 8/2019 | Mclaughlin |
| 10,369,002 | B2 | 8/2019 | Rhoda et al. |
| 10,376,373 | B2 | 8/2019 | Howard |
| 10,390,960 | B2 | 8/2019 | Bannigan |
| 10,413,421 | B2 | 9/2019 | Arnold |
| 10,433,973 | B2 | 10/2019 | Howard |
| 10,492,928 | B2 | 12/2019 | Himmelberger |
| 10,500,057 | B2 | 12/2019 | Mclaughlin |
| 10,537,437 | B2 | 1/2020 | Josse |
| 10,624,759 | B2 | 4/2020 | Stinchfield |
| 10,646,352 | B2 | 5/2020 | Mclaughlin |
| 10,675,155 | B2 | 6/2020 | Prevost |
| 10,687,956 | B2 | 6/2020 | Ullrich, Jr. |
| 10,758,365 | B2 | 9/2020 | Cummins |
| 10,806,595 | B2 | 10/2020 | Refai |
| 10,869,766 | B2 | 12/2020 | Hansell et al. |
| 11,291,551 | B2 | 4/2022 | Hansell et al. |
| 11,357,641 | B2 | 6/2022 | Stinchfield |
| 11,399,951 | B2 | 8/2022 | Hansell |
| 11,564,803 | B2 | 1/2023 | McLaughlin et al. |

| | | | |
|---|---|---|---|
| 2001/0047208 | A1 | 11/2001 | Michelson |
| 2002/0026196 | A1 | 2/2002 | Simon |
| 2002/0028192 | A1 | 3/2002 | Dimitrijevich |
| 2002/0055782 | A1 | 5/2002 | Bagby |
| 2002/0120274 | A1 | 8/2002 | Overaker |
| 2002/0143330 | A1 | 10/2002 | Shluzas |
| 2002/0143400 | A1 | 10/2002 | Biscup |
| 2002/0169448 | A1 | 11/2002 | Vanacker |
| 2003/0018334 | A1 | 1/2003 | Richelsoph |
| 2003/0023306 | A1 | 1/2003 | Liu |
| 2003/0028192 | A1 | 2/2003 | Manuel |
| 2003/0065396 | A1 | 4/2003 | Michelson |
| 2003/0093035 | A1 | 5/2003 | Mohammed |
| 2003/0125739 | A1 | 7/2003 | Bagga |
| 2003/0167091 | A1 | 9/2003 | Scharf |
| 2003/0167092 | A1 | 9/2003 | Foley |
| 2003/0171813 | A1 | 9/2003 | Kiester |
| 2003/0176925 | A1 | 9/2003 | Paponneau |
| 2003/0176926 | A1 | 9/2003 | Boehm |
| 2003/0181981 | A1 | 9/2003 | Lemaire |
| 2003/0191531 | A1 | 10/2003 | Berry |
| 2003/0191535 | A1 | 10/2003 | Castro |
| 2003/0195626 | A1 | 10/2003 | Huppert |
| 2003/0195629 | A1 | 10/2003 | Pafford |
| 2003/0195632 | A1 | 10/2003 | Foley |
| 2003/0199980 | A1 | 10/2003 | Siedler |
| 2003/0199983 | A1 | 10/2003 | Michelson |
| 2004/0010315 | A1 | 1/2004 | Song |
| 2004/0019356 | A1 | 1/2004 | Fraser |
| 2004/0030387 | A1 | 2/2004 | Landry |
| 2004/0034358 | A1 | 2/2004 | Michelson |
| 2004/0034430 | A1 | 2/2004 | Falahee |
| 2004/0049271 | A1 | 3/2004 | Biedermann |
| 2004/0054412 | A1 | 3/2004 | Gerbec |
| 2004/0059419 | A1 | 3/2004 | Michelson |
| 2004/0059420 | A1 | 3/2004 | Michelson |
| 2004/0064185 | A1 | 4/2004 | Michelson |
| 2004/0068259 | A1 | 4/2004 | Michelson |
| 2004/0073314 | A1 | 4/2004 | White et al. |
| 2004/0078078 | A1 | 4/2004 | Shepard |
| 2004/0078079 | A1 | 4/2004 | Foley |
| 2004/0082999 | A1 | 4/2004 | Mathys |
| 2004/0088054 | A1 | 5/2004 | Berry |
| 2004/0093083 | A1 | 5/2004 | Branch |
| 2004/0093084 | A1 | 5/2004 | Michelson |
| 2004/0093085 | A1 | 5/2004 | Michelson |
| 2004/0093086 | A1 | 5/2004 | Michelson |
| 2004/0097928 | A1 | 5/2004 | Zdeblick |
| 2004/0097929 | A1 | 5/2004 | Branch |
| 2004/0102848 | A1 | 5/2004 | Michelson |
| 2004/0117017 | A1 | 6/2004 | Pasquet |
| 2004/0117018 | A1 | 6/2004 | Michelson |
| 2004/0133280 | A1 | 7/2004 | Trieu |
| 2004/0153156 | A1 | 8/2004 | Cohen et al. |
| 2004/0153160 | A1 | 8/2004 | Carrasco |
| 2004/0186569 | A1 | 9/2004 | Berry |
| 2004/0210312 | A1 | 10/2004 | Neumann |
| 2004/0236427 | A1 | 11/2004 | Berry |
| 2005/0010294 | A1 | 1/2005 | Michelson |
| 2005/0015097 | A1 | 1/2005 | Mujwid |
| 2005/0049706 | A1 | 3/2005 | Brodke |
| 2005/0085910 | A1 | 4/2005 | Sweeney |
| 2005/0090898 | A1 | 4/2005 | Berry |
| 2005/0096745 | A1 | 5/2005 | Andre |
| 2005/0107878 | A1 | 5/2005 | Conchy |
| 2005/0113921 | A1 | 5/2005 | An |
| 2005/0131419 | A1 | 6/2005 | Mccord |
| 2005/0159813 | A1 | 7/2005 | Molz |
| 2005/0209697 | A1 | 9/2005 | Paponneau et al. |
| 2005/0216088 | A1 | 9/2005 | Mckinley |
| 2005/0228377 | A1 | 10/2005 | Chao |
| 2005/0234550 | A1 | 10/2005 | Metz-Stavenhagen |
| 2005/0283236 | A1 | 12/2005 | Razian |
| 2006/0058877 | A1 | 3/2006 | Gutlin |
| 2006/0058879 | A1 | 3/2006 | Metz-Stavenhagen |
| 2006/0074490 | A1 | 4/2006 | Sweeney |
| 2006/0100710 | A1 | 5/2006 | Gutlin |
| 2006/0116770 | A1 | 6/2006 | White |
| 2006/0195095 | A1 | 8/2006 | Meuller et al. |

(56) References Cited

U.S. PATENT DOCUMENTS

| | | | |
|---|---|---|---|
| 2006/0200244 A1 | 9/2006 | Assaker | |
| 2006/0241762 A1 | 10/2006 | Kraus | |
| 2007/0028710 A1 | 2/2007 | Kraus | |
| 2007/0255407 A1* | 11/2007 | Castleman | A61F 2/44 |
| | | | 606/279 |
| 2008/0161933 A1* | 7/2008 | Grotz | A61F 2/4465 |
| | | | 623/17.11 |
| 2008/0167720 A1 | 7/2008 | Melkent | |
| 2008/0243254 A1 | 10/2008 | Butler | |
| 2008/0288071 A1 | 11/2008 | Biyani | |
| 2011/0087328 A1 | 4/2011 | Dickson | |
| 2011/0138948 A1* | 6/2011 | Jimenez | F16H 25/20 |
| | | | 74/424.82 |
| 2011/0178598 A1* | 7/2011 | Rhoda | A61F 2/4465 |
| | | | 623/17.16 |
| 2012/0232660 A1* | 9/2012 | Davenport | A61F 2/44 |
| | | | 623/17.16 |
| 2014/0277509 A1 | 9/2014 | Robinson | |
| 2015/0018953 A1 | 1/2015 | Frasier | |
| 2017/0079807 A1* | 3/2017 | Wallenstein | A61F 2/44 |
| 2017/0105850 A1 | 4/2017 | Howard | |
| 2018/0116813 A1 | 5/2018 | Richter | |
| 2018/0243078 A1* | 8/2018 | Jastifer | A61F 2/0811 |
| 2019/0000645 A1 | 1/2019 | Stinchfield | |
| 2019/0125545 A1 | 5/2019 | Refai | |
| 2019/0151108 A1 | 5/2019 | Schröter | |
| 2019/0167438 A1 | 6/2019 | Hansell et al. | |
| 2019/0231557 A1 | 8/2019 | Sutterlin, III | |
| 2019/0247200 A1 | 8/2019 | Ulrich, Jr. | |
| 2019/0254837 A1 | 8/2019 | Hansell | |
| 2019/0269523 A1 | 9/2019 | Wallenstein | |
| 2019/0328542 A1 | 10/2019 | Bannigan | |
| 2019/0358055 A1 | 11/2019 | Arnold | |
| 2020/0000604 A1 | 1/2020 | Howard | |
| 2020/0054463 A1 | 2/2020 | Himmelberger | |
| 2020/0078187 A1 | 3/2020 | Mclaughlin | |
| 2020/0261236 A1 | 8/2020 | Prevost | |
| 2021/0145599 A1 | 5/2021 | Howard | |
| 2021/0330470 A1* | 10/2021 | Dewey | A61F 2/446 |
| 2022/0023066 A1* | 1/2022 | Howard | A61F 2/4611 |
| 2022/0401227 A1 | 12/2022 | Semler et al. | |

FOREIGN PATENT DOCUMENTS

| | | | |
|---|---|---|---|
| DE | 2750648 | A1 | 5/1979 |
| DE | 3023942 | A1 | 1/1982 |
| DE | 3741487 | A1 | 6/1989 |
| DE | 4012622 | C1 | 7/1991 |
| DE | 4323595 | C1 | 7/1994 |
| DE | 19500170 | C1 | 2/1996 |
| DE | 19604246 | A1 | 8/1996 |
| DE | 19622827 | A1 | 12/1997 |
| EP | 0179695 | A1 | 4/1986 |
| EP | 0290767 | A1 | 11/1988 |
| EP | 0369603 | A1 | 5/1990 |
| EP | 0490159 | A1 | 6/1992 |
| EP | 0517030 | A2 | 12/1992 |
| EP | 0706876 | A1 | 4/1996 |
| EP | 0716840 | A2 | 6/1996 |
| EP | 0796593 | A2 | 9/1997 |
| EP | 0880938 | A1 | 12/1998 |
| EP | 1039855 | A1 | 10/2000 |
| EP | 1077659 | A1 | 2/2001 |
| EP | 1080703 | A2 | 3/2001 |
| EP | 1100417 | A1 | 5/2001 |
| EP | 1121075 | A1 | 8/2001 |
| EP | 1334703 | A2 | 8/2003 |
| EP | 1346709 | A2 | 9/2003 |
| EP | 1391188 | A1 | 2/2004 |
| EP | 1391189 | A1 | 2/2004 |
| EP | 1398008 | A1 | 3/2004 |
| EP | 1400221 | A2 | 3/2004 |
| EP | 1410770 | A1 | 4/2004 |
| EP | 1415622 | A1 | 5/2004 |
| EP | 1415623 | A1 | 5/2004 |
| EP | 1430857 | A1 | 6/2004 |
| EP | 1430858 | A1 | 6/2004 |
| JP | 2003305068 | A | 10/2003 |
| WO | 9106261 | A1 | 5/1991 |
| WO | 9201428 | A1 | 2/1992 |
| WO | 9404100 | A1 | 3/1994 |
| WO | 9418913 | A1 | 9/1994 |
| WO | 9501810 | A1 | 1/1995 |
| WO | 9608205 | A1 | 3/1996 |
| WO | 9640020 | A1 | 12/1996 |
| WO | 9641582 | A1 | 12/1996 |
| WO | 9733525 | A1 | 9/1997 |
| WO | 9809586 | A1 | 3/1998 |
| WO | 9814142 | A1 | 4/1998 |
| WO | 9817208 | A2 | 4/1998 |
| WO | 9834552 | A1 | 8/1998 |
| WO | 9907312 | A1 | 2/1999 |
| WO | 9908627 | A1 | 2/1999 |
| WO | 9932054 | A1 | 7/1999 |
| WO | 9932055 | A1 | 7/1999 |
| WO | 9938461 | A2 | 8/1999 |
| WO | 9956675 | A1 | 11/1999 |
| WO | 0007527 | A1 | 2/2000 |
| WO | 0023013 | A1 | 4/2000 |
| WO | 0106962 | A1 | 2/2001 |
| WO | 0209786 | A2 | 2/2002 |
| WO | 0219952 | A1 | 3/2002 |
| WO | 0238086 | A1 | 5/2002 |
| WO | 02060356 | A1 | 8/2002 |
| WO | 02076335 | A2 | 10/2002 |
| WO | 02078514 | A2 | 10/2002 |
| WO | 03009786 | A1 | 2/2003 |
| WO | 03013399 | A1 | 2/2003 |
| WO | 03020143 | A1 | 3/2003 |
| WO | 03026522 | A2 | 4/2003 |
| WO | 03026538 | A1 | 4/2003 |
| WO | 03068112 | A1 | 8/2003 |
| WO | 03096937 | A1 | 11/2003 |
| WO | 04000177 | | 12/2003 |
| WO | 04008999 | | 1/2004 |
| WO | 04024038 | | 3/2004 |
| WO | 04026188 | | 4/2004 |
| WO | 04041130 | | 5/2004 |
| WO | 04043306 | | 5/2004 |
| WO | 04052245 | | 6/2004 |

OTHER PUBLICATIONS thespinemarketgroup.com; 6 Expandable Corpectomy Devices to Know . . . ! Published Dec. 3, 2020.

The International Bureau of WIPO; International Preliminary Report on Patentability issued in PCT/US2022/077611 on Apr. 9, 2024.

* cited by examiner

60

See Fig. 18

EXPANDABLE VERTEBRAL IMPLANT AND METHOD

CROSS-REFERENCE TO RELATED APPLICATIONS

This application is a nonprovisional patent application of and claims priority and benefit under 35 U.S.C. § 119 to U.S. Provisional Application No. 63/253,784, filed Oct. 8, 2021, the entire contents of which are hereby incorporated by reference.

TECHNICAL FIELD

The present embodiments relate generally to spinal implants.

BACKGROUND

The spine is formed of a column of vertebrae that extends between the cranium and pelvis. The three major sections of the spine are known as the cervical, thoracic, and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the pelvic region of the vertebral column. These fused vertebrae consist of the sacral and coccygeal region of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g. walking, talking, and breathing). Therefore, it is of great interest and concern to be able to both correct and prevent any ailments of the spine.

Trauma to the spine (e.g. car accident, sports injury) can cause fracturing of one or more vertebrae. Certain diseases affecting the spine (e.g. tumors, osteoporosis) can cause degeneration of the spine. Both trauma and degeneration may result in severe disruption to the spine. In these circumstances, the complete removal of one or more vertebrae may be required. If one or more vertebrae are removed, a replacement support system must be implanted in order to protect the spinal cord and maintain, or improve, the structure and integrity of the spine.

The present invention is directed at overcoming, or at least improving upon, the disadvantages of the prior art.

SUMMARY

In some embodiments of the invention, for example, a spinal implant may include an expandable body configured to expand from a first end to a second end along a longitudinal axis. In various embodiments, the expandable body may have an outer core, a middle core, and an inner core threadedly coupled and moveable relative to each other along the longitudinal axis. In some embodiments, the middle core may be configured to both rotate about and translate along the longitudinal axis to adjust a relative location of the outer core to the inner core thereby adjusting a body length of the expandable body.

In some embodiments, the spinal implant may include a connecting sleeve, wherein the connecting sleeve translates along the longitudinal axis and/or does not allow rotation of the inner core relative to the outer core. In various embodiments, the sleeve/structure/member may be one or more internal/external members that engage the outer core and the inner core and does not allow rotation of the inner core relative to the outer core. In various embodiments, the middle core may include a plurality of gear teeth or recesses. In some embodiments, the plurality of gear teeth or recesses may be in a helical pattern about a periphery of the middle core. In various embodiments, the middle core may be threadedly coupled to both the inner core and the outer core. In some embodiments, the middle core may have an outer periphery with a first thread and an inner periphery with a second thread, wherein the inner core may include an outer periphery with a third thread, and wherein the outer core includes an inner periphery with a fourth thread. In various embodiments, the first thread and the second thread may be different, wherein the first thread runs in a different direction than the second thread. In some embodiments, the inner core may include a hollow interior portion and a threaded external portion, and a first end portion may be configured to engage a first vertebral body. In various embodiments, the outer core may include a hollow threaded interior portion coaxially configured to receive the middle core and the inner core therein, and a second end portion configured to engage a second vertebral body. In some embodiments, the middle core may include a hollow threaded portion coaxially configured to receive the inner core therein and a threaded external portion configured to engage the hollow interior portion of the outer core. In various embodiments, the middle core may include a plurality of gear teeth or recesses cut into at least a portion of an outer periphery. In some embodiments, one or more locking mechanisms may be configured to engage the outer core with the middle core and/or the inner core. In various embodiments, the one or more locking mechanisms may be configured to translate along the longitudinal axis. In various embodiments, one or more locking mechanisms may be a connecting sleeve locking the rotation about the longitudinal axis of the inner core with respect to the outer core. In some embodiments, the one or more locking mechanisms may be a locking member and/or biasing member. In various embodiments, at least one of a first end portion of the inner core and a second end portion of the outer core may comprise a first attachment feature; one or more endplates coupled to the implant with the first attachment feature in at least one of the first end and the second end. In some embodiments, a polyaxial endplate assembly may be attached to at least one of the inner core and the outer core. In some embodiments, the polyaxial endplate assembly may be capable of pivoting along at least two intersecting axes disposed in the same plane which is not parallel to the longitudinal axis. In various embodiments, the polyaxial endplate assembly may include a collar clamp and/or a locking member. In some embodiments, a counterbore may extend through an inner surface and an opposite outer surface of the outer core; a first set screw positioned in the counterbore to fix the inner core and/or middle core relative to the outer core. In various embodiments, the spinal implant may include a biased locking member to fix the rotation of the middle core and/or inner core relative to the outer core. In some embodiments, the biased locking member may include one or more locking teeth and one or more biasing element.

In various embodiments, a method for inserting the spinal implant may include positioning the spinal implant in a patient's spine. In some embodiments, the method may include rotating the middle core to cause the spinal implant to expand from a first length to a second length, wherein said second length is greater than the first length.

In various embodiments, an implant may include an expandable body configured to expand from a first end to a second end along a longitudinal axis. In some embodiments, the expandable body may have at least one rotatable member configured to rotate about the longitudinal axis to adjust a relative location of the first end and second end of the expandable body thereby adjusting a body length of the expandable body. In various embodiments, a plurality of gear teeth or recesses are cut into an outer surface of at least one rotatable member about the longitudinal axis. In some embodiments, an outer member may be dynamically coupled to the rotatable member. In various embodiments, a locking mechanism may be dynamically coupled to the outer member that includes an engagement member protruding medially towards the longitudinal axis. In some embodiments, the locking mechanism may be configured to have a locked state and unlocked state, wherein in the locked state, the engagement member is configured to be engaged with one or several of the plurality of gear teeth or recesses of at least one rotatable member, thereby fixing at least one rotatable member with respect to the outer member, thereby fixing the body length of the expandable body, and in the unlocked state, the engagement member is configured to be disengaged from at least one rotatable member, thereby allowing at least one rotatable member to rotate, thereby allowing the body length of the expandable body to be adjusted.

In addition, in some embodiments, at least one rotatable member may be a middle core. In various embodiments, the implant may include an inner core. In some embodiments, the locking mechanism may include one or more biasing members urging the engagement member towards the one or several of the plurality of gear teeth or recesses of at least one rotatable member. In various embodiments, the one or more biasing members may include one or more leaf springs. In some embodiments, the locking mechanism may translate along the longitudinal direction between the locked state and the unlocked state. In various embodiments, the outer surface of at least one rotatable member may include one or more threads, wherein the one or more threads includes the plurality of gear teeth or recesses. In various embodiments, the implant may be in combination with an inserter, wherein coupling the inserter to the implant moves the locking mechanism and/or the engagement member from the locked state to the unlocked state, and decoupling the inserter from the implant moves the locking mechanism and/or the engagement member from the unlocked state to the locked state.

In various embodiments, a spinal implant may include a body or assembly extending between a first end and a second end along a longitudinal axis. In some embodiments, the spinal implant may include a polyaxial endplate assembly attached to at least one of the first end and the second end. In various embodiments, the polyaxial endplate assembly may comprise an articulatable plate, a flexible collar member, and a locking member. In some embodiments, the articulatable plate may be capable of pivoting along at least two intersecting axes disposed in the same plane which is not parallel to the longitudinal axis of the implant. In various embodiments, the articulatable plate includes an endplate and a rounded body extending from the endplate. In some embodiments, the flexible collar member may extend around at least a portion of a circumference of the body of the articulatable plate. In various embodiments, the locking member may be dynamically coupled with the flexible collar member and configured to apply radial compression to at least a portion of the circumference of the endplate, thereby fixing the articulatable plate with respect to the body or assembly.

In addition, in some embodiments, the locking member may be offset away from the longitudinal axis. In various embodiments, the locking member may be a set screw. In some embodiments, the spinal implant may include a fixed endplate on the other one of the first end and the second end not attached to the polyaxial endplate assembly. In various embodiments, the spinal implant may be configured to facilitate two distinct degrees of freedom to allow articulation of the rounded body relative to at least one first end or the second end. In some embodiments, the endplate may include a top wall, wherein the top wall includes a substantially planar surface oriented transverse to the longitudinal axis and movable relative to an orientation of a vertebra or tissue. In various embodiments, the rounded body may include a plurality of first steps. In some embodiments, the flexible collar member may include a plurality of second steps. In various embodiments, the rounded body may include a spherical surface.

In various embodiments, a polyaxial endplate assembly may include an articulatable plate having an endplate and a rounded body extending from the endplate. In some embodiments, the rounded body may be configured to be received within a clamping assembly of an implant. In various embodiments, the body may be articulatable relative to the clamping assembly. In some embodiments, the clamping assembly may be disposed circumferentially around and over the body of the articulatable plate. In various embodiments, the clamping assembly may have a flexible collar member with one fixed end relative to the clamping assembly and one free end, a locking member dynamically coupled with the flexible collar member and configured to press against the free end of the flexible collar member, thereby applying radial compression to at least a portion of the body of the articulatable plate, thereby fixing the endplate with respect to the clamping assembly.

In addition, in some embodiments, the locking member may be offset away from a longitudinal axis of the implant. In various embodiments, the locking member may be a set screw, wherein the set screw may be received in a counterbore within the clamping assembly. In some embodiments, the spinal implant may include a fixed endplate on the implant opposite to the articulatable plate. In various embodiments, the spinal implant may include a modular endplate coupling to at least one of the fixed endplate and the articulatable plate.

BRIEF DESCRIPTION OF THE ILLUSTRATIONS

In the drawings, like reference characters generally refer to the same parts throughout the different views. Also, the drawings are not necessarily to scale, emphasis instead generally being placed upon illustrating the principles of the invention.

Figure 1:
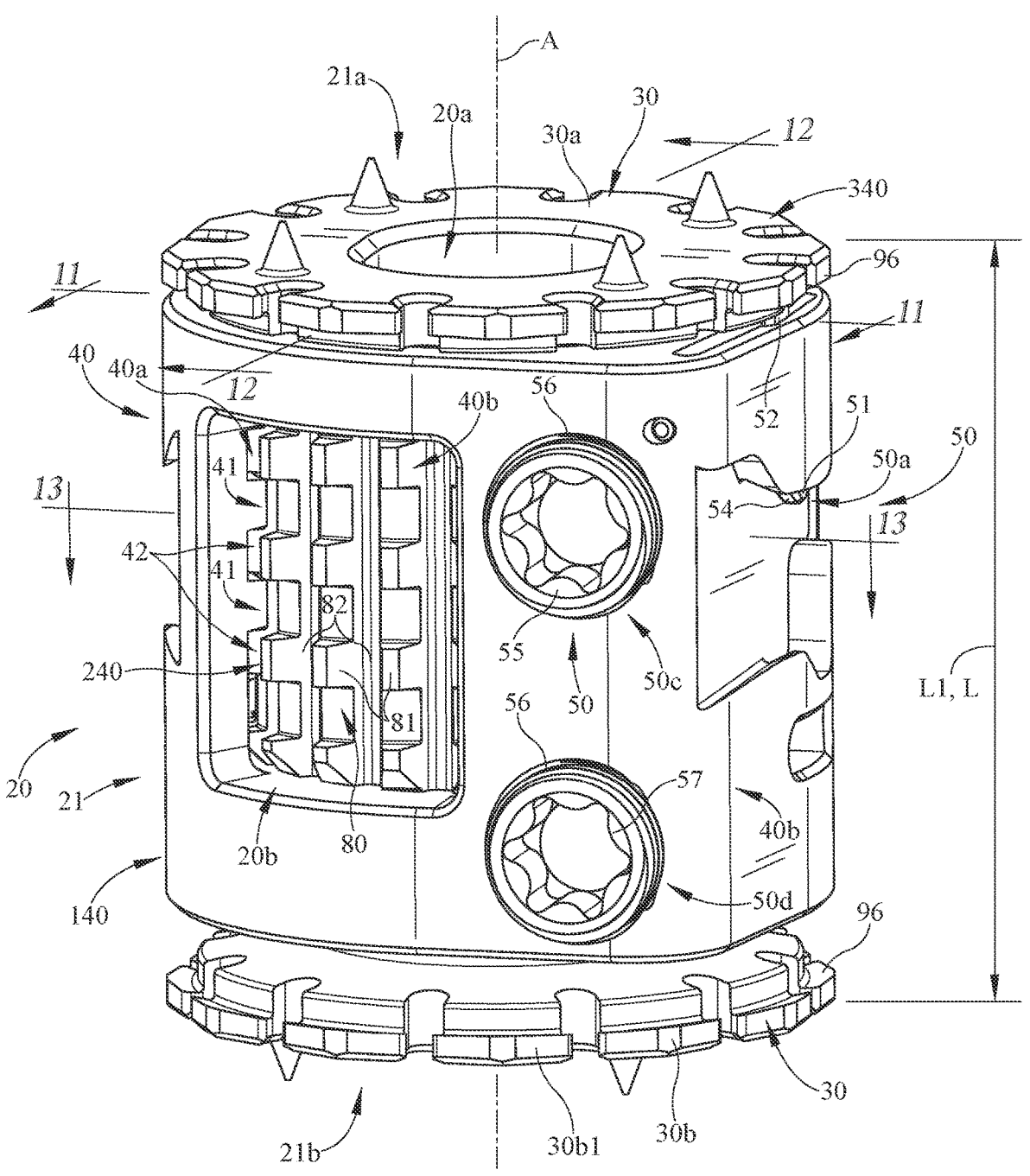
FIG. 1 is a perspective view of the expandable spinal implant illustrating the implant according to an embodiment having a first length.
Figure 15:
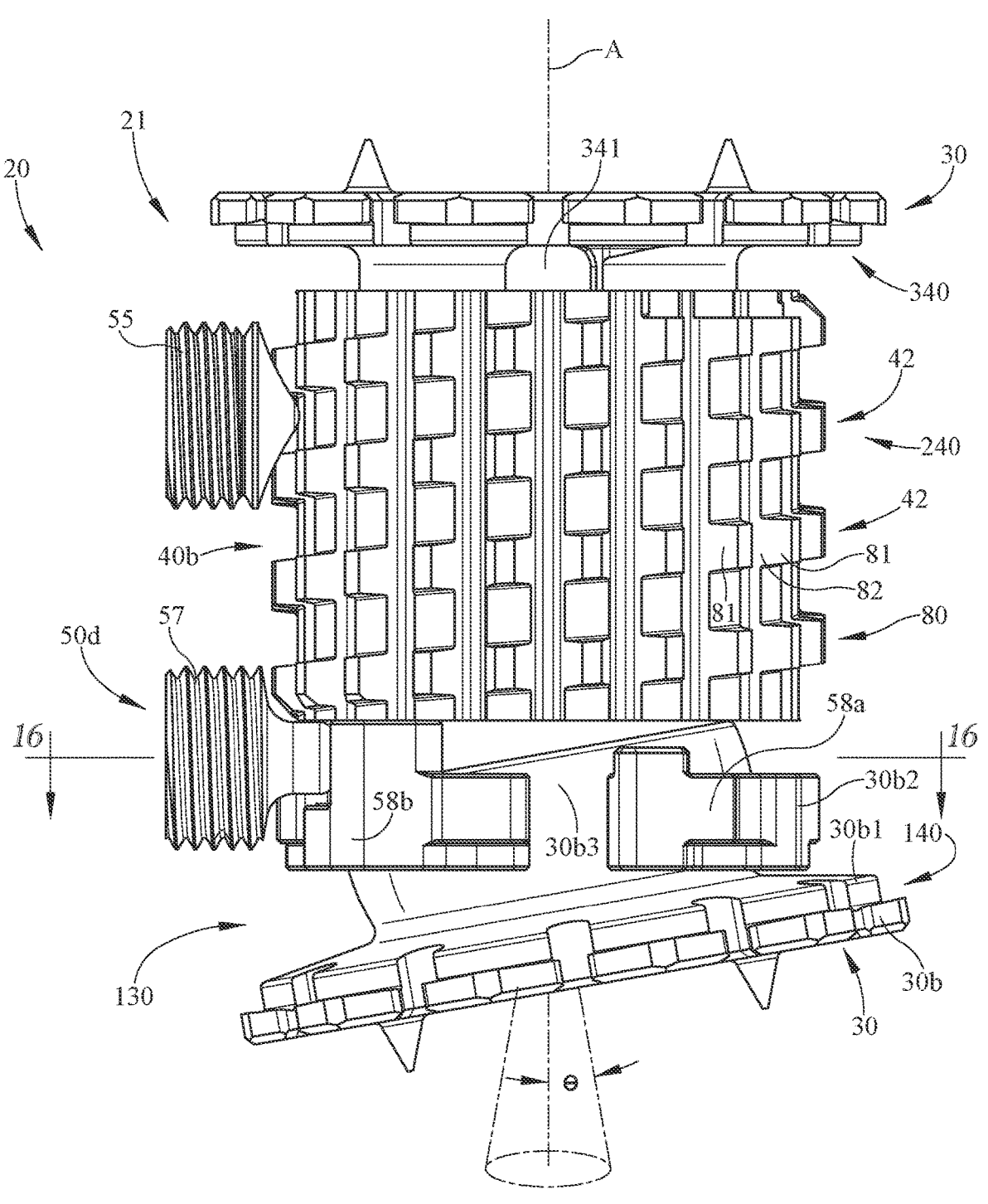

FIG. 15 a side view of the implant of FIG. 1 illustrating the articulation endplate angled away from the position of FIG. 1 with the outer core broken away.

Figure 16:
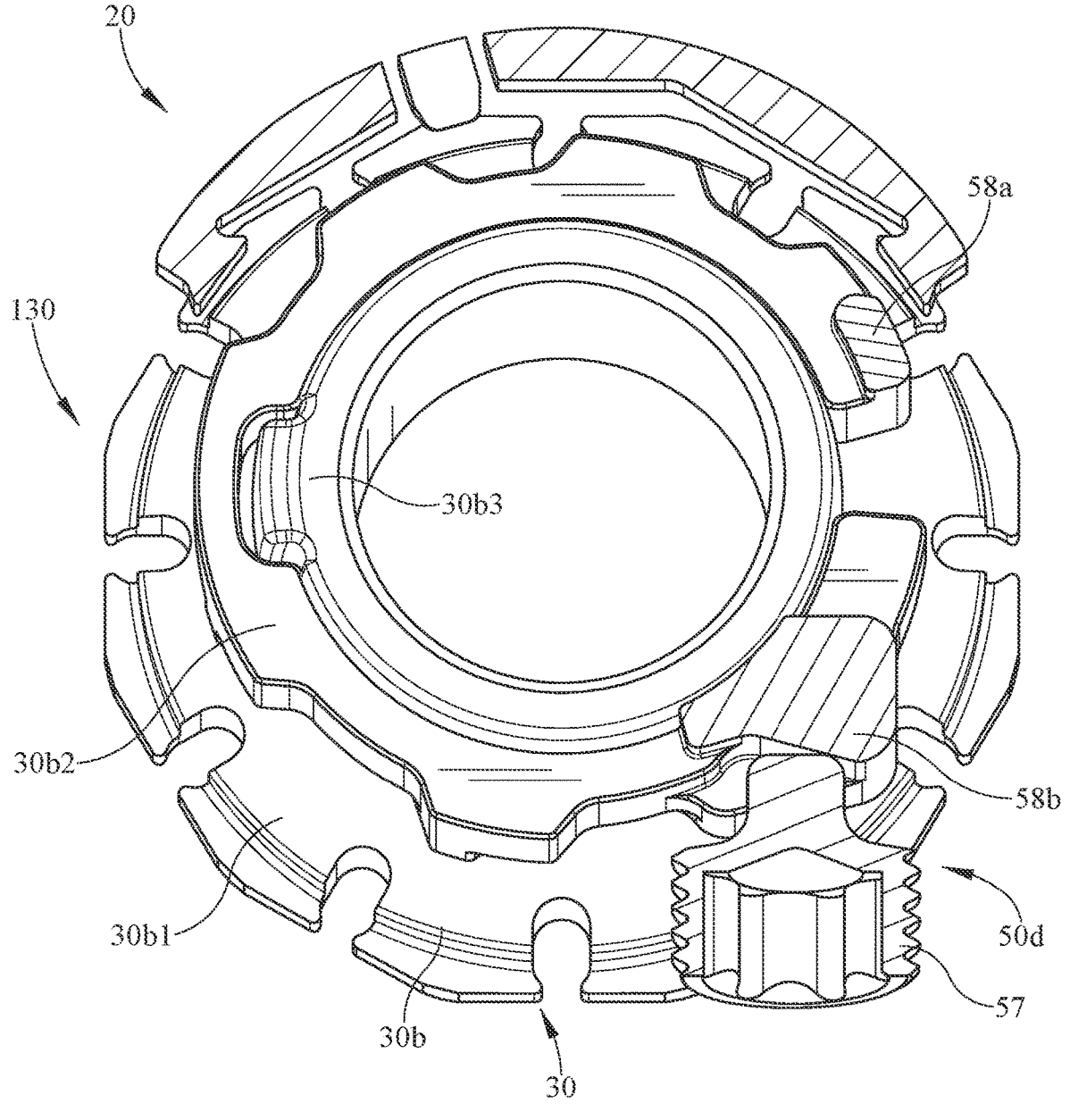

FIG. 16 is a sectional view of the implant of FIG. 15 taken along line 16-16.

Figure 17:
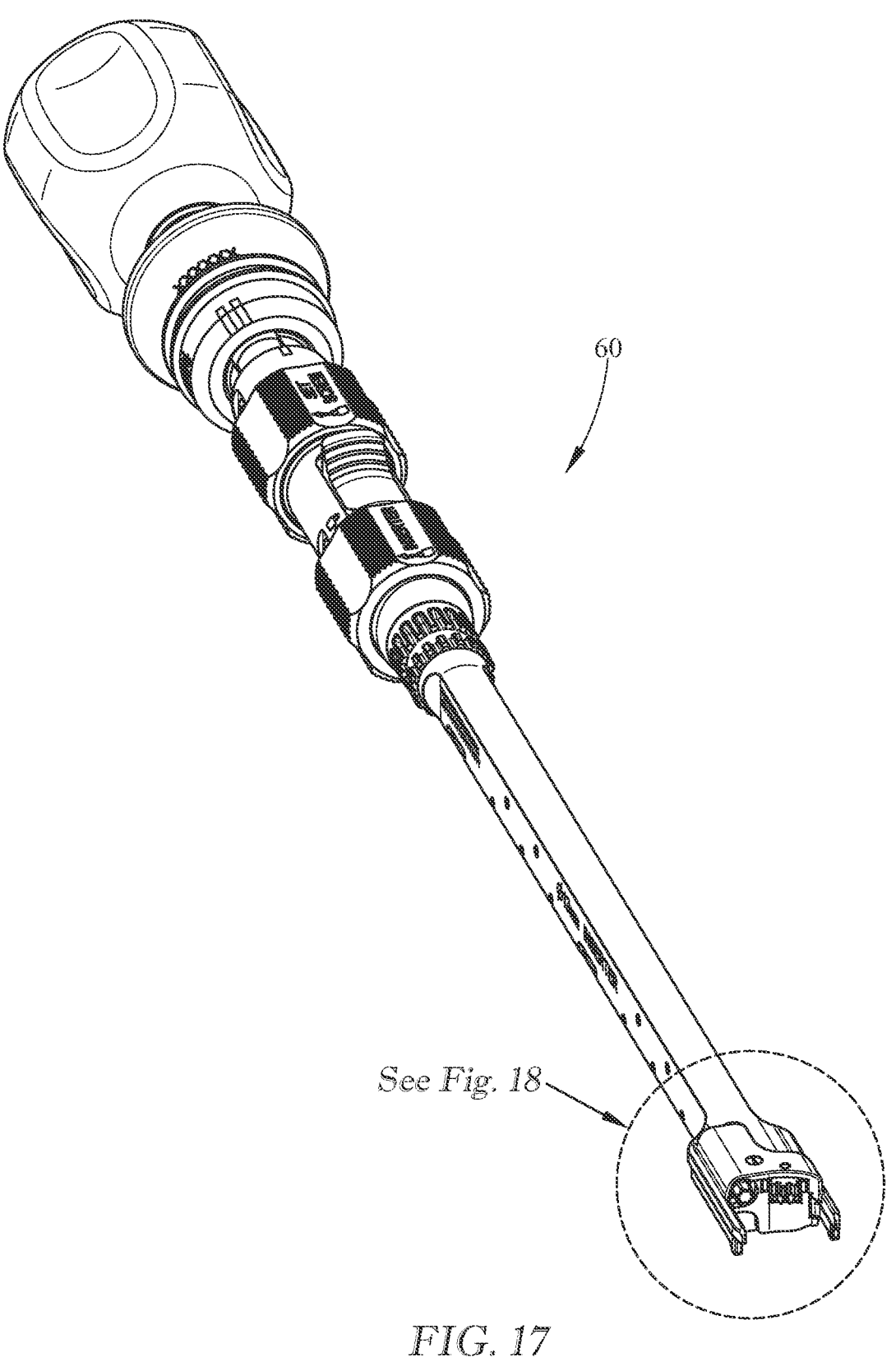

FIG. 17 is a perspective view of an inserter.

Figure 18:
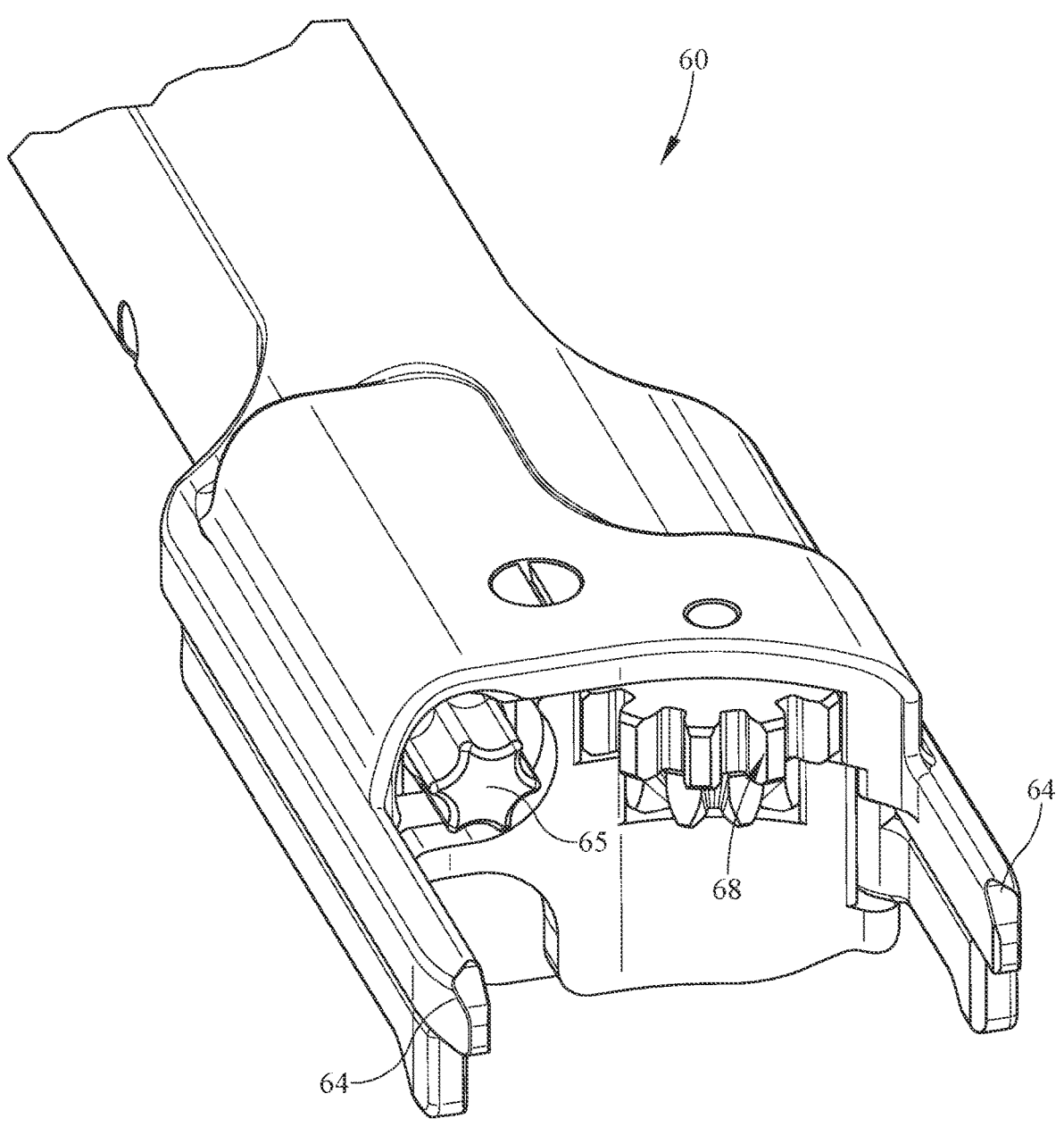

FIG. 18 is an enlarged view of the inserter of FIG. 17.

Figure 19:
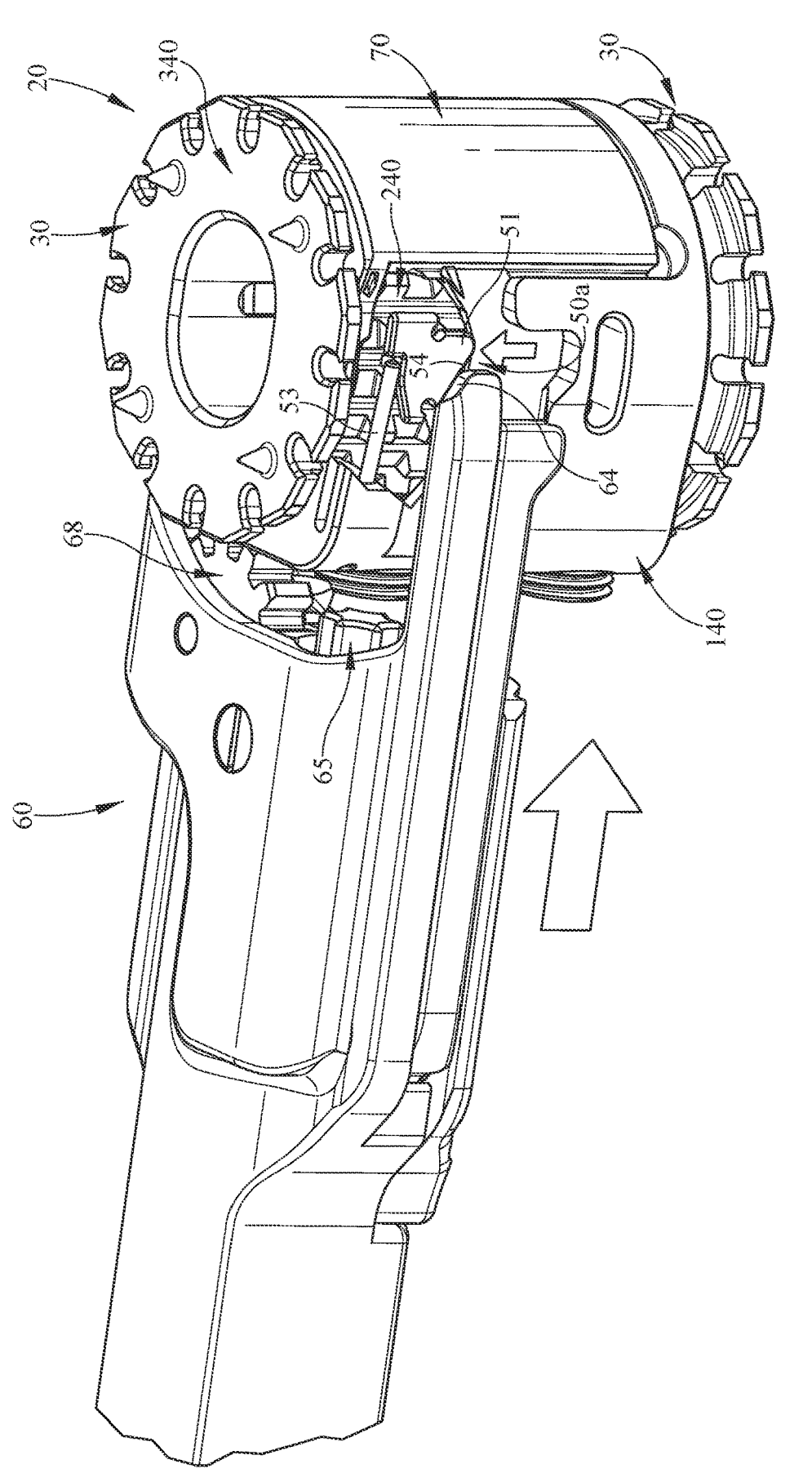

FIG. 19 is a perspective view of the inserter and implant, illustrating coupling the inserter with the implant and the first locking mechanism in the locked state.

Figure 20:
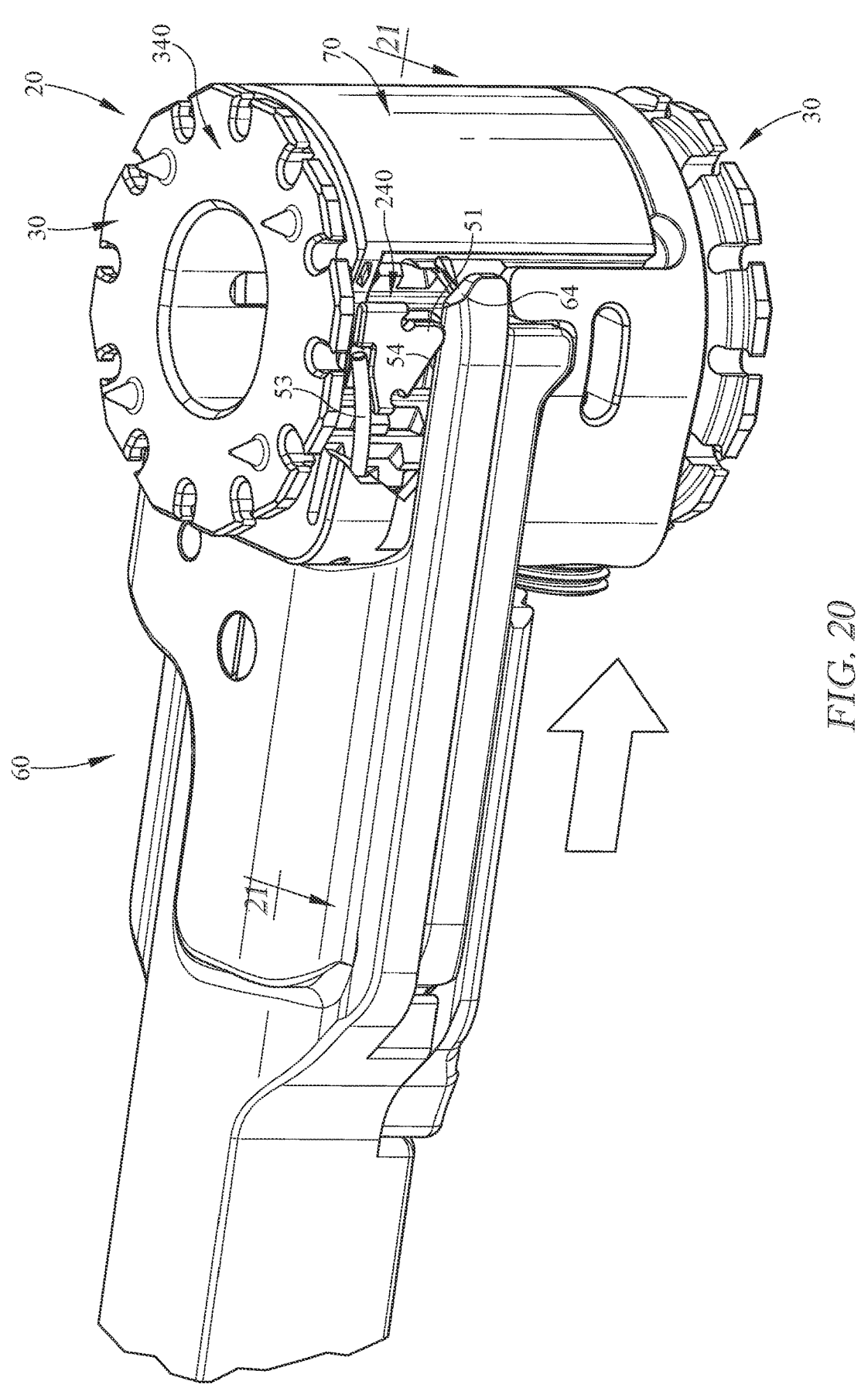

FIG. 20 is a perspective view of the inserter and implant, illustrating coupling the inserter with the implant and the first locking mechanism in the unlocked state.

Figure 21:
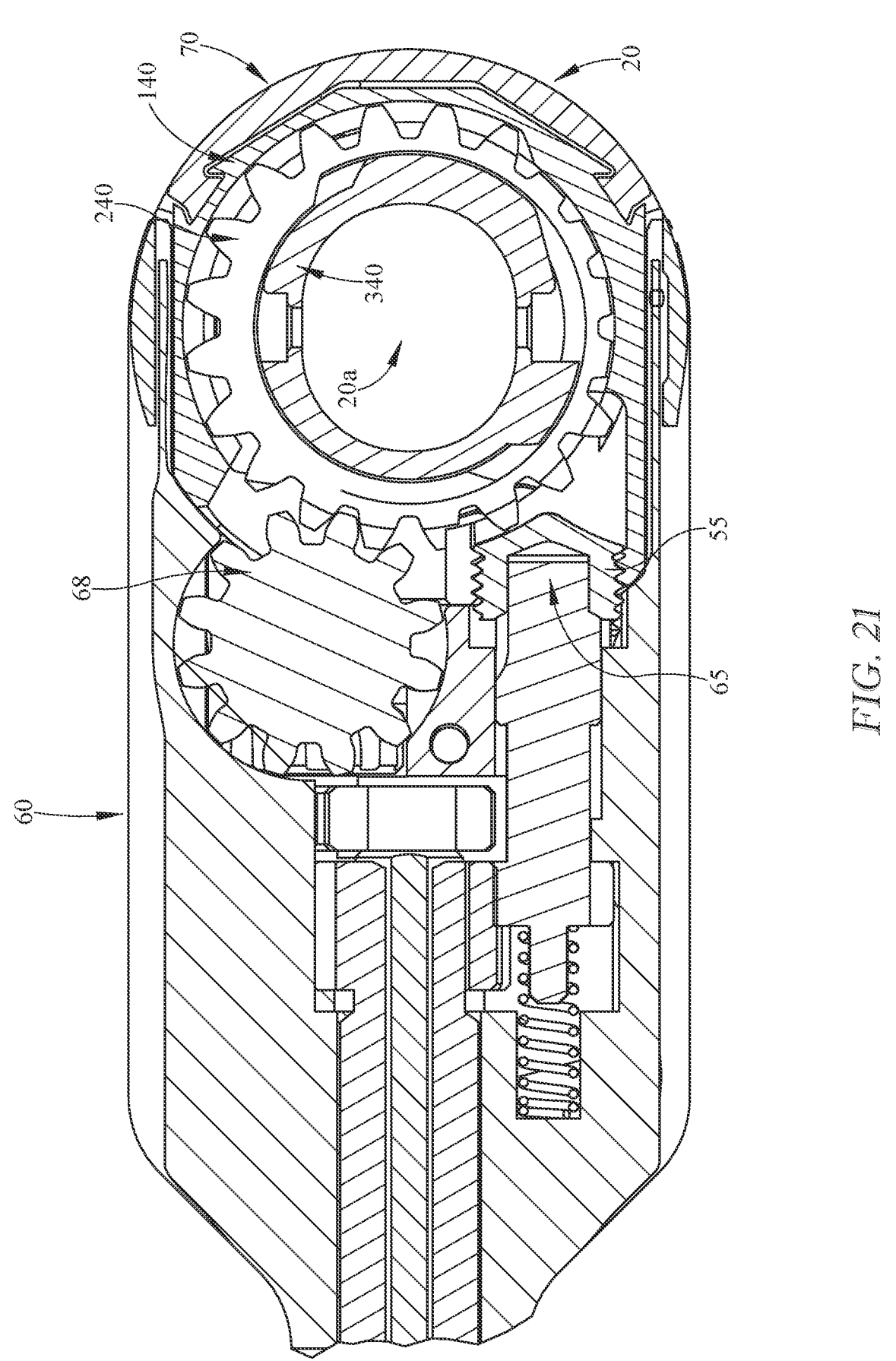

FIG. 21 is a section view of the inserter and implant taken along line 21-21 of FIG. 20, illustrating coupling the gear of the inserter with the middle core or gear teeth and/or recesses.

Figure 22:
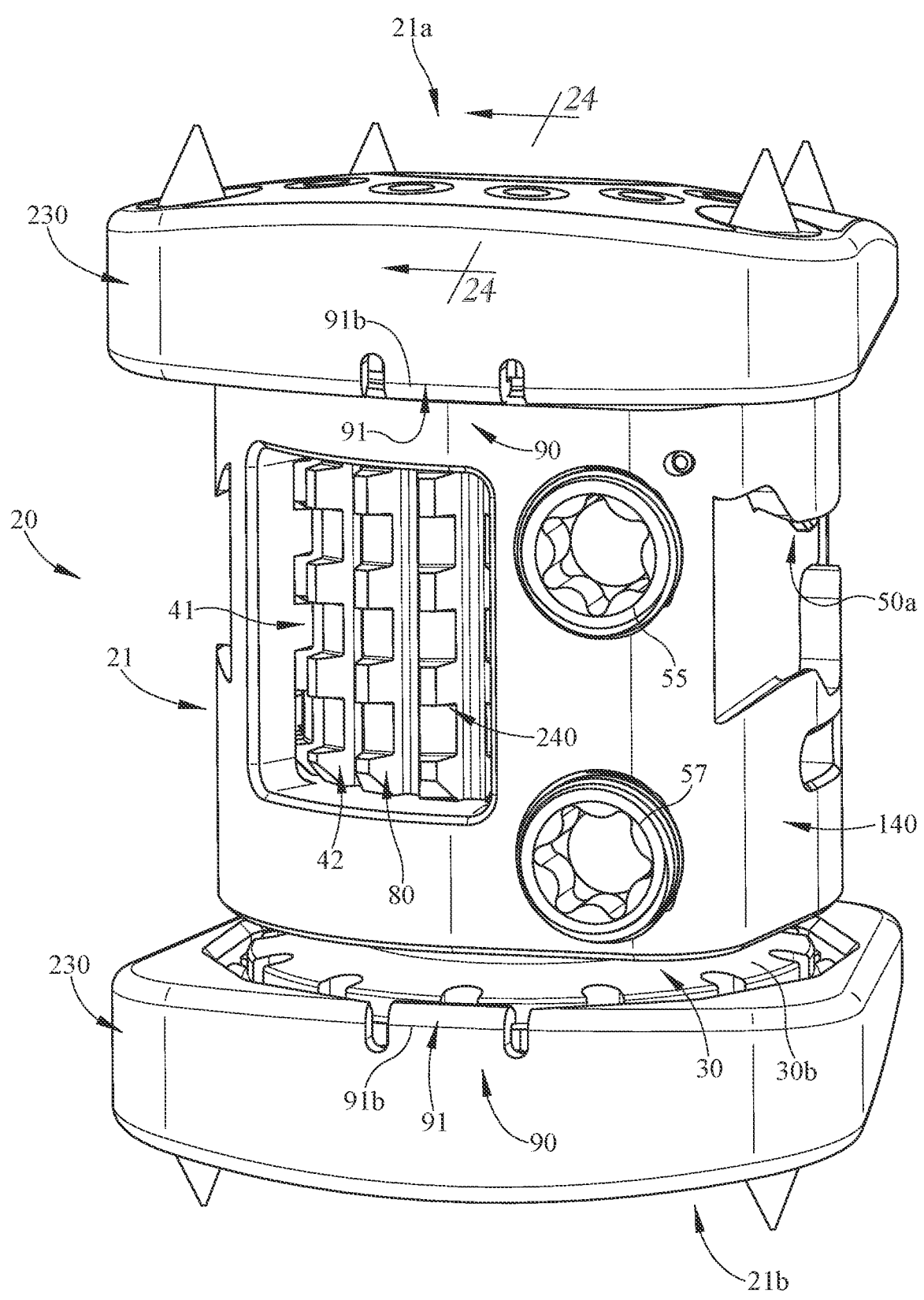

FIG. 22 is a perspective view of the implant of FIG. 1 illustrating one or more modular endplates attached to one or more ends of the implant.

Figure 23:
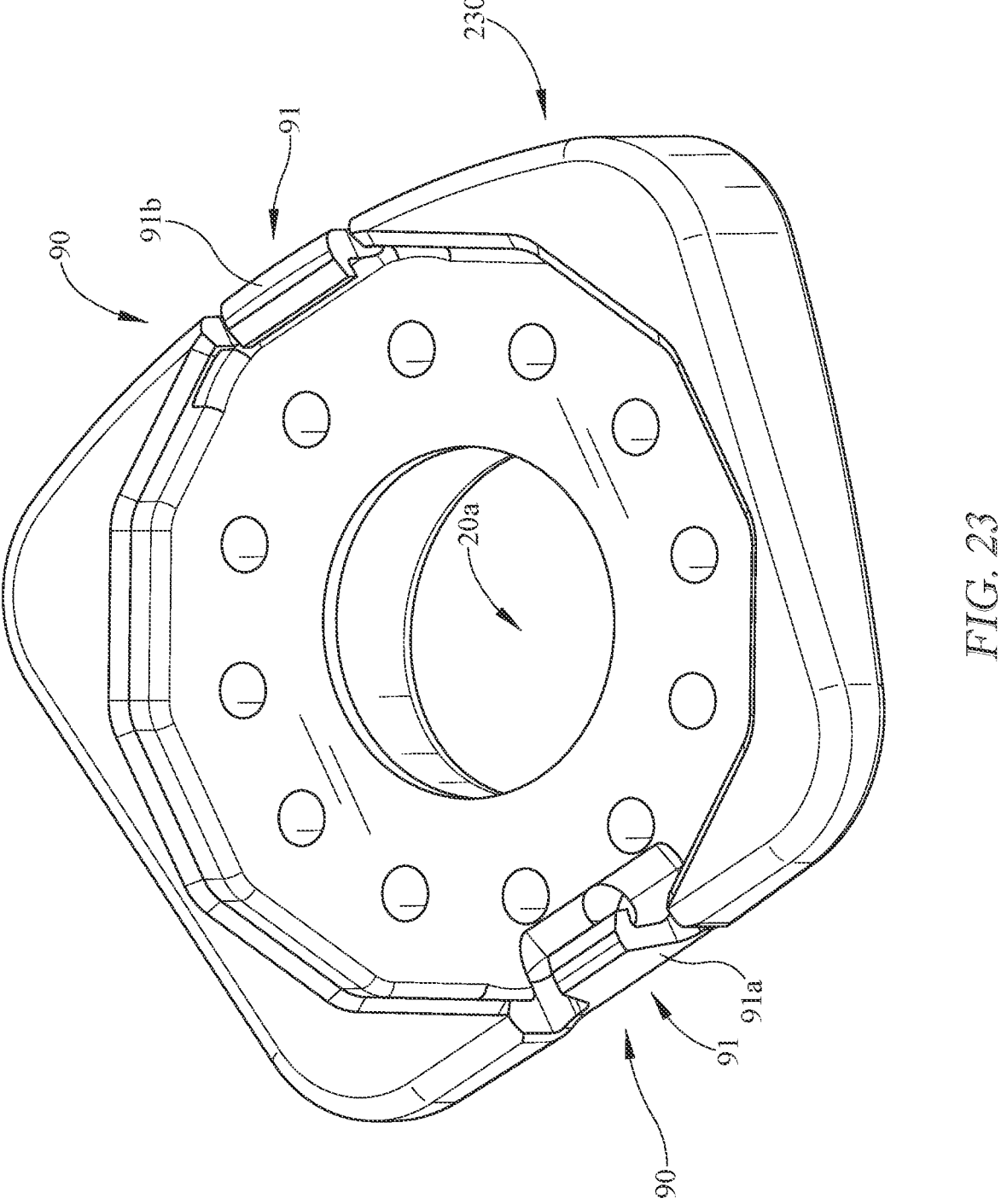

FIG. 23 is a perspective view of the modular endplate.

Figures 24, 25:
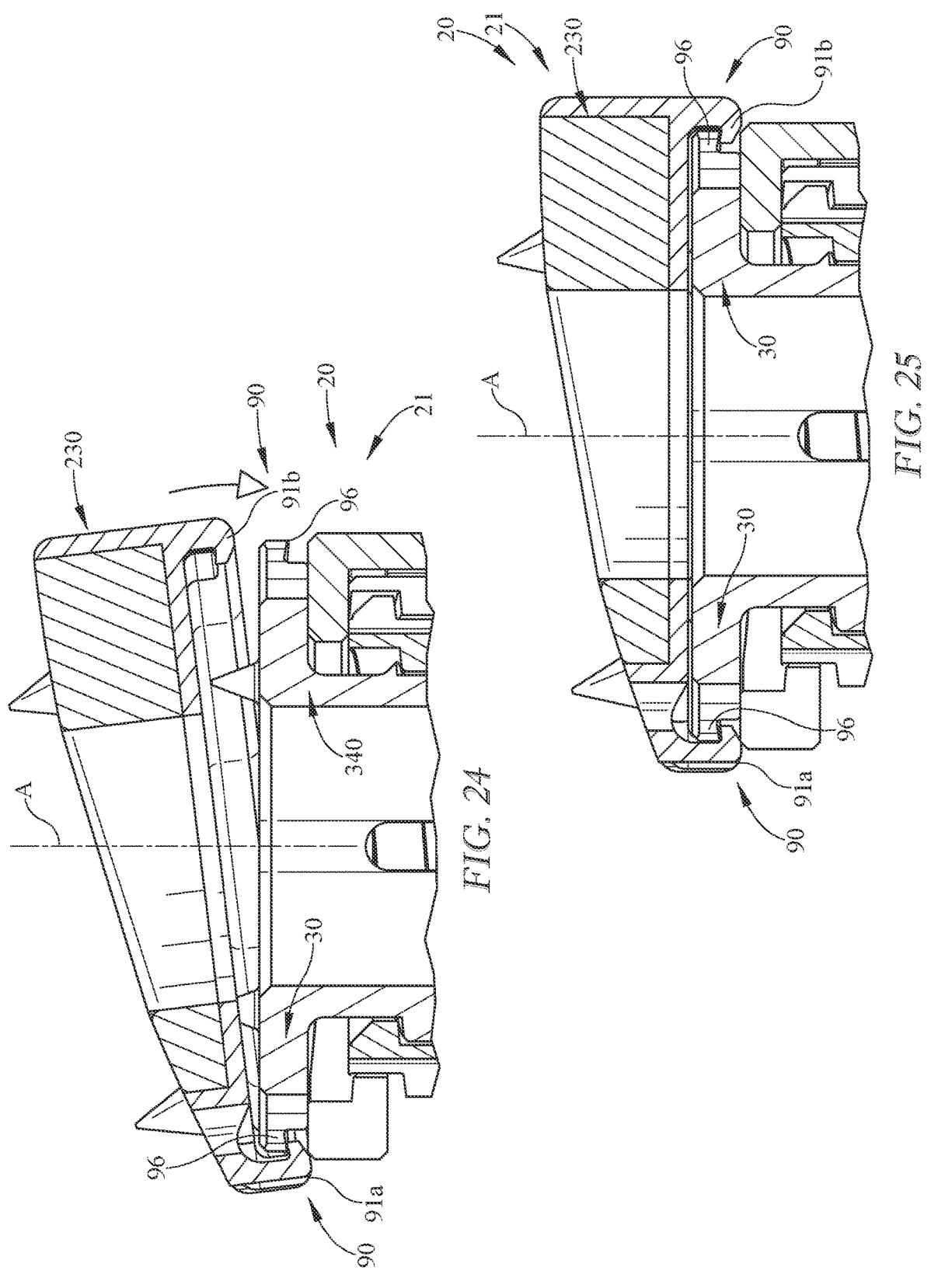

FIG. 24 is a sectional view taken along line 24-24 of FIG. 22, illustrating the static hook under the lip of the integrated endplate.

FIG. 25 is a sectional view taken along line 24-24 of FIG. 22, illustrating the static hook under the lip of the integrated endplate and rotated down to engage the flexible hook outward under the opposite lip of the integrated endplate, securing the modular endplate to the core.

Figure 26:
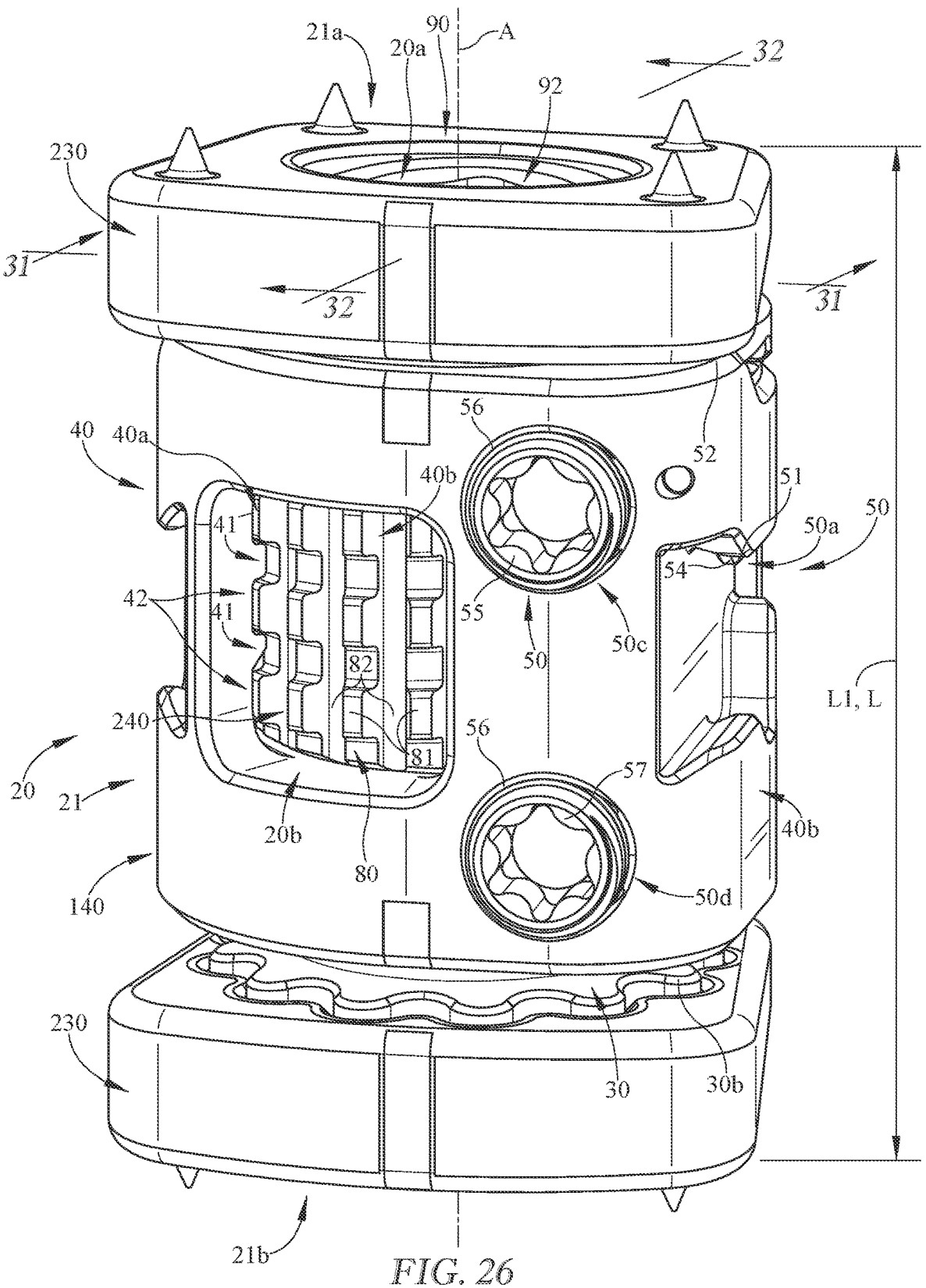

FIG. 26 is a perspective view of the expandable spinal implant illustrating the implant according to an embodiment having a first length.

Figure 27:
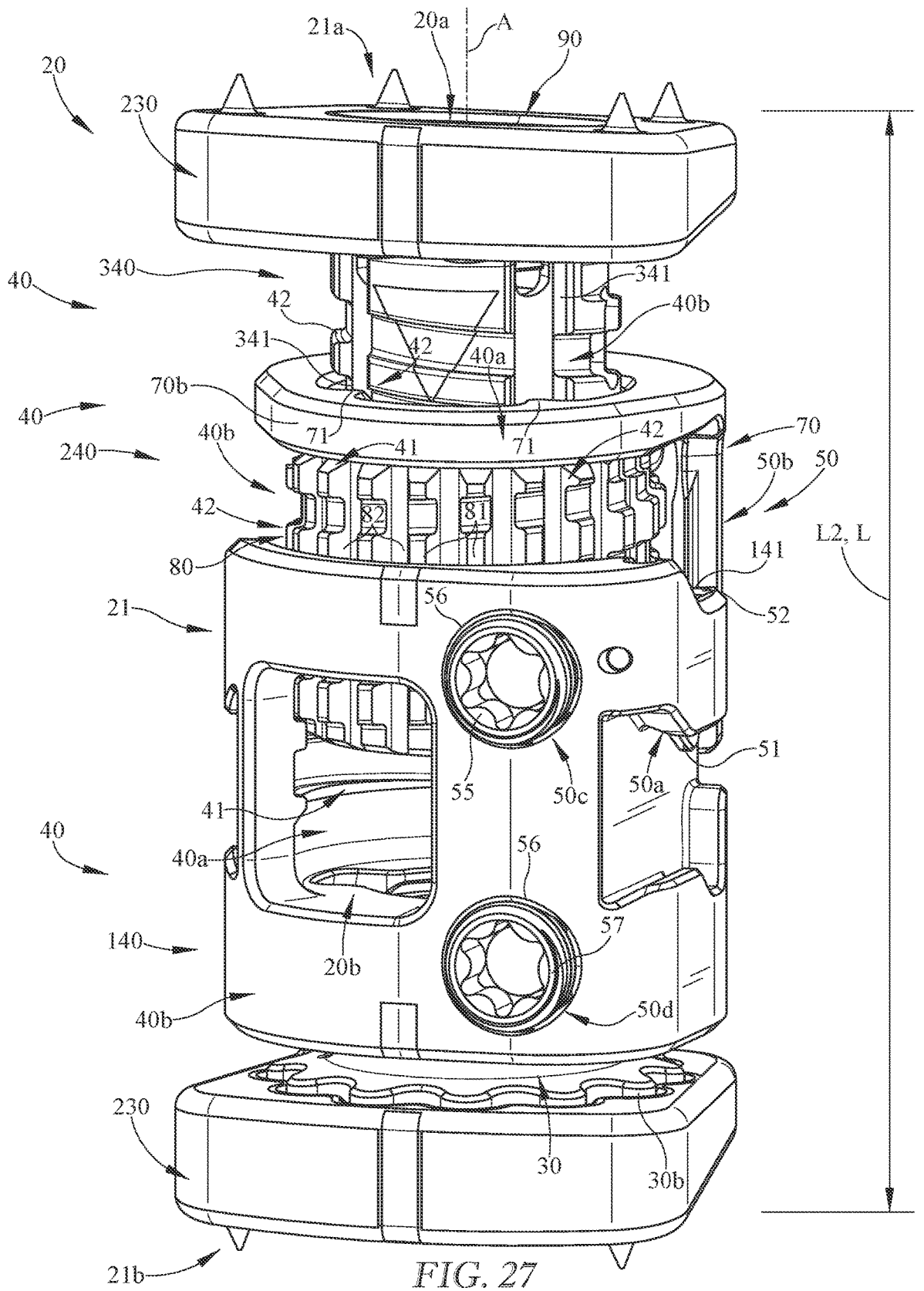

FIG. 27 is a perspective view of the implant of FIG. 26 illustrating the implant occupying a second length larger than the first length.

Figure 28:
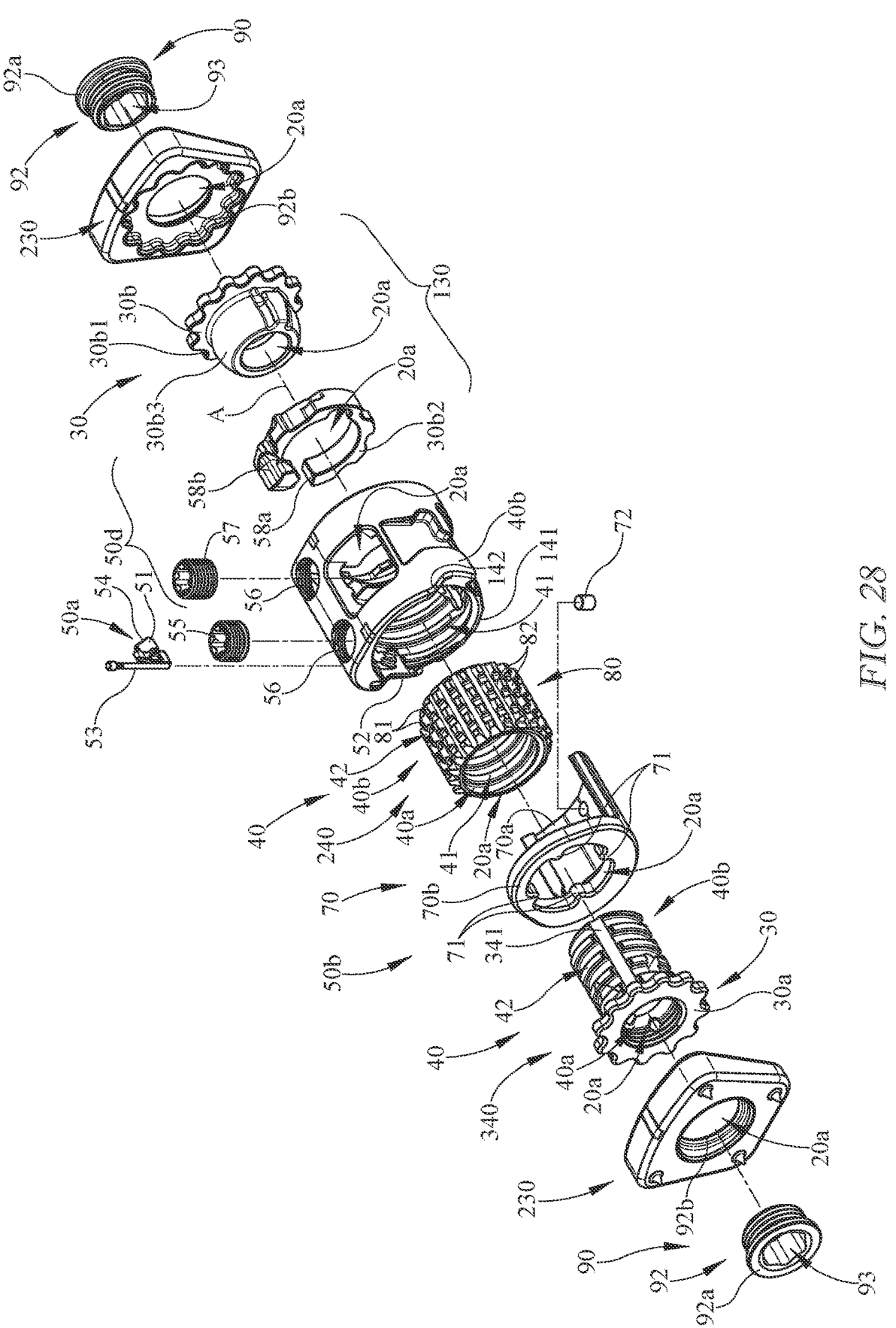

FIG. 28 is an exploded view of the spinal implant of FIG. 26.

Figure 29:
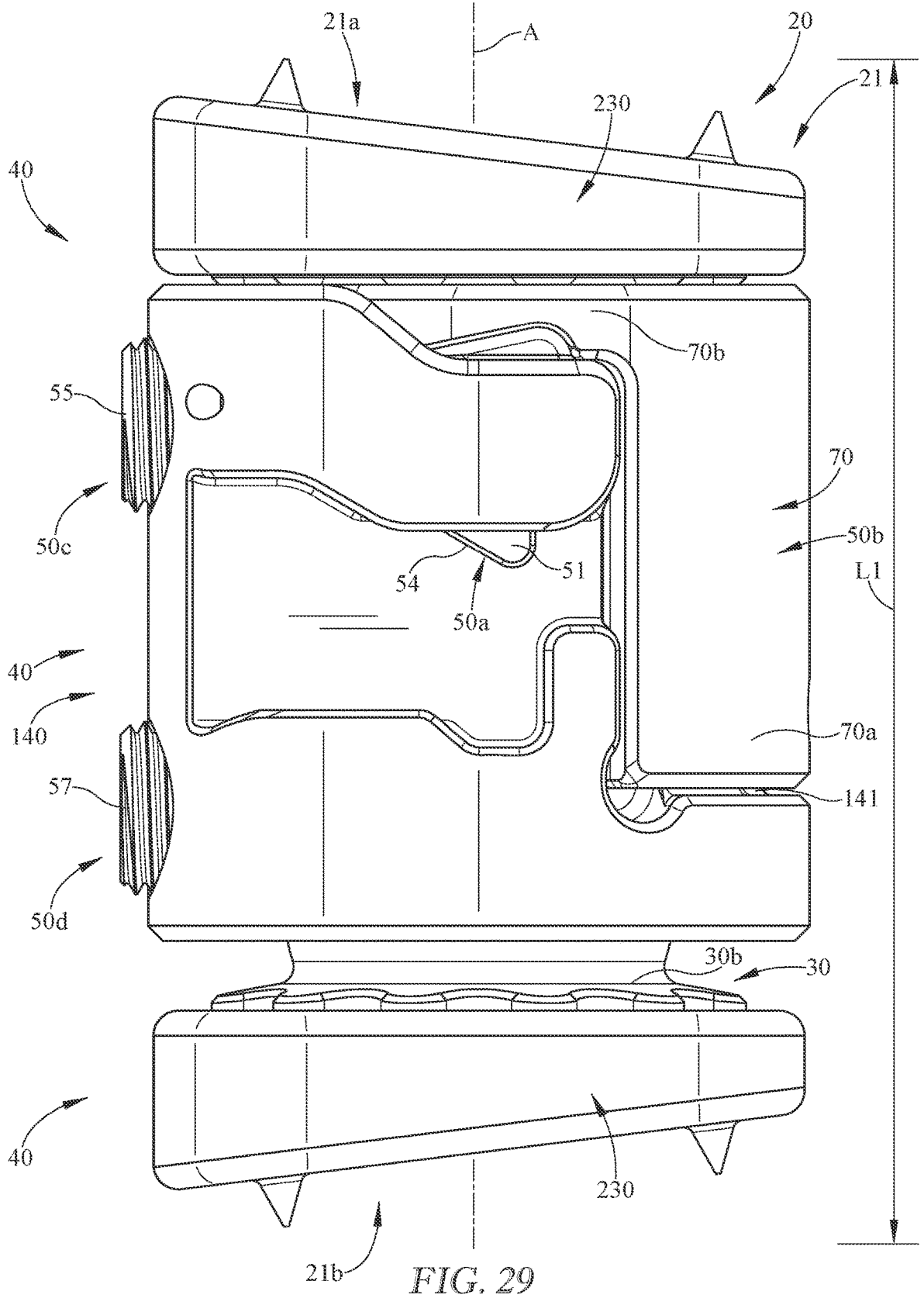

FIG. 29 is side view of the implant of FIG. 26 illustrating the implant in the first length.

Figure 30:
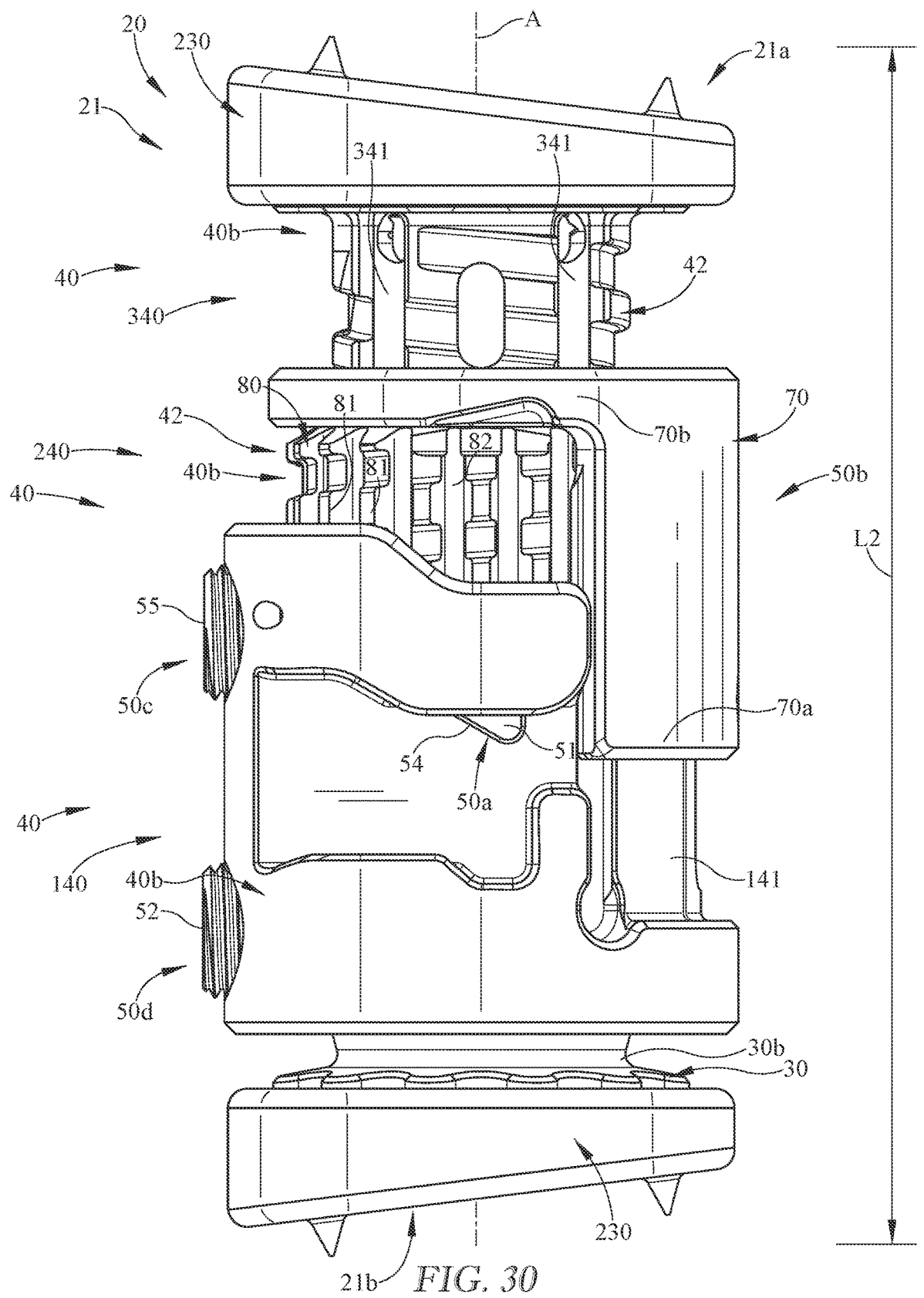

FIG. 30 is side view of the implant of FIG. 27 illustrating the implant in the second length.

Figure 31:
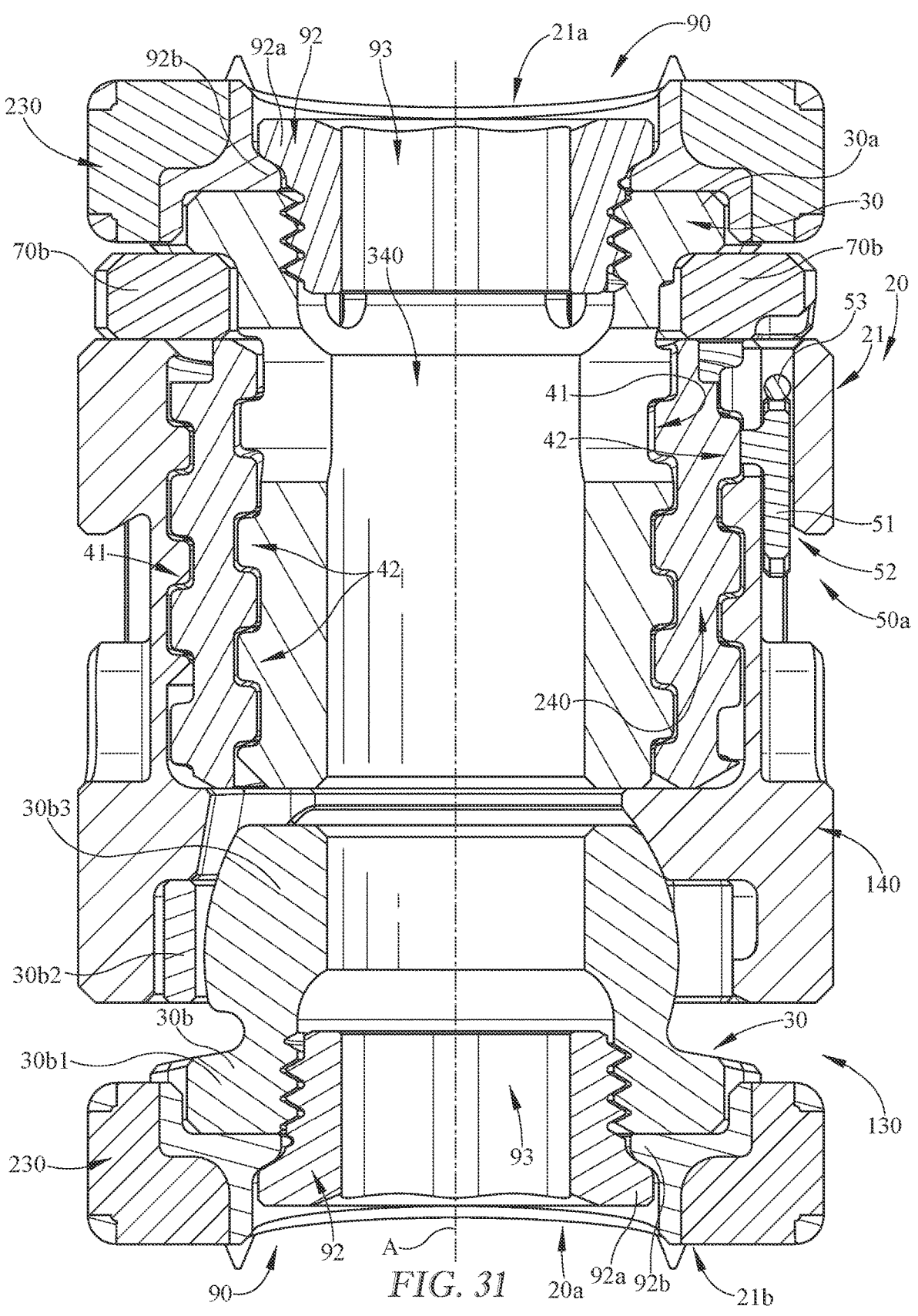

FIG. 31 is a sectional view of the implant of FIG. 26 taken along line 31-31.

Figure 32:
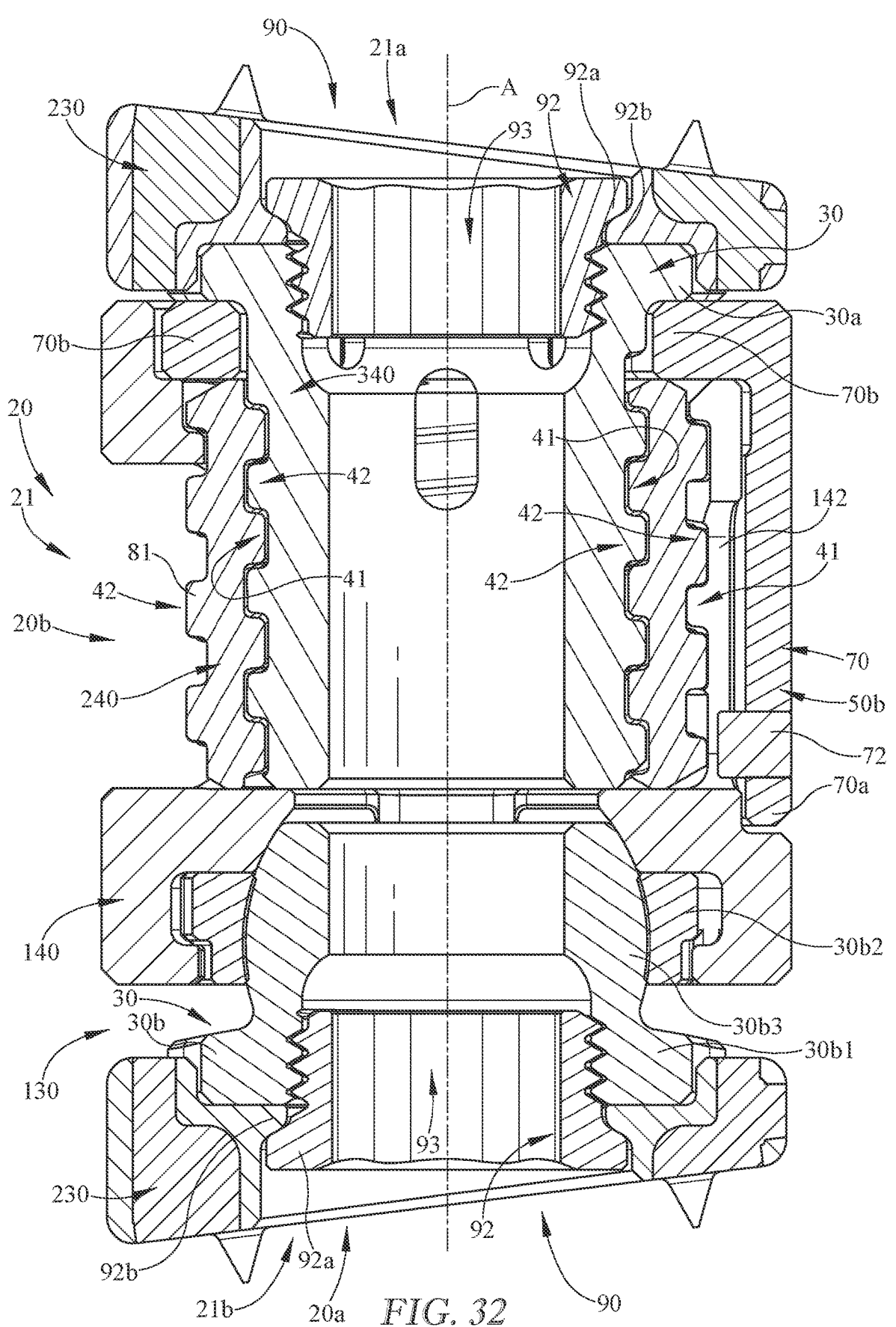

FIG. 32 is a sectional view of the implant of FIG. 26 taken along line 32-32.

Figure 33:
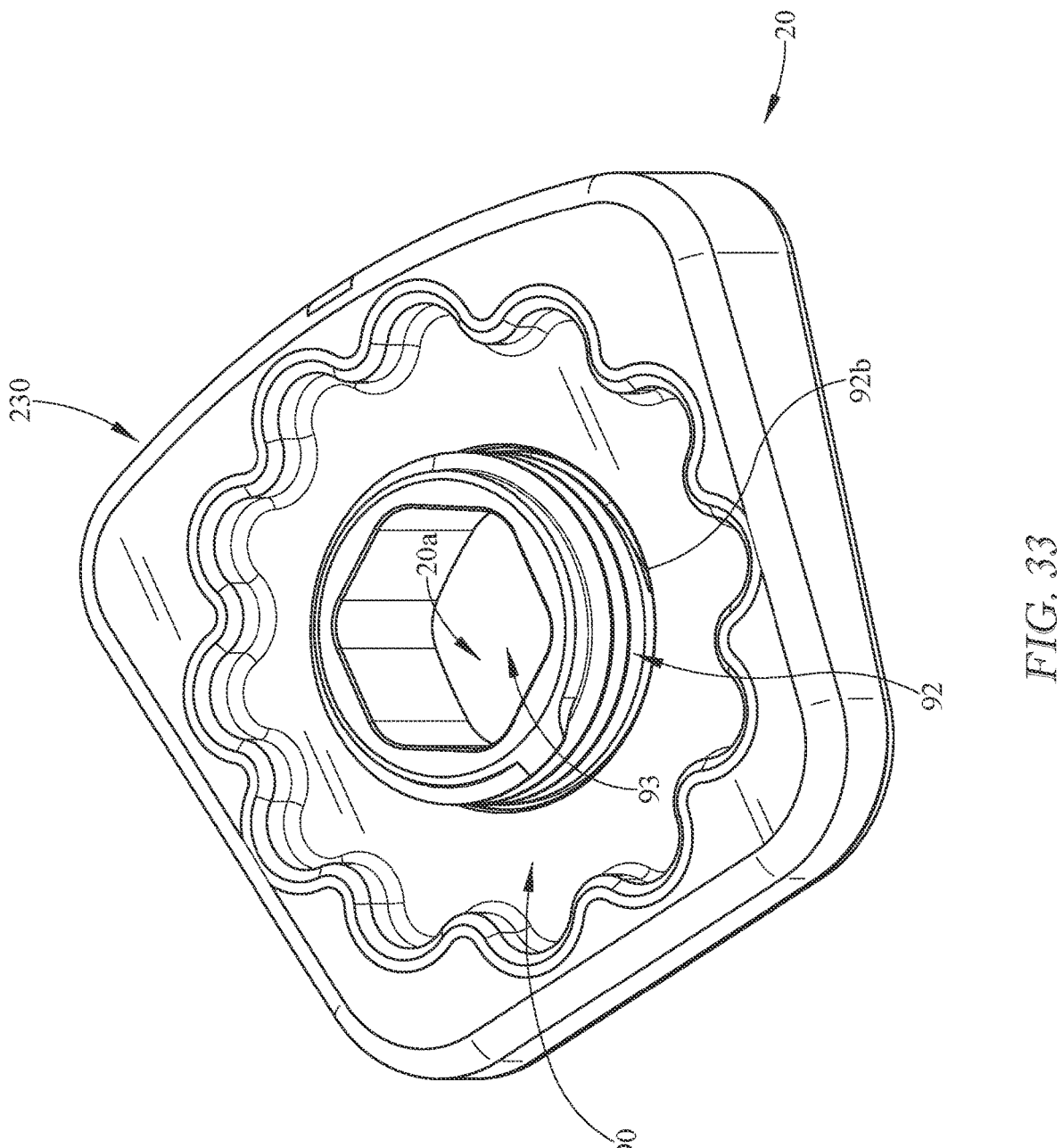

FIG. 33 is a perspective view of the modular endplate of FIG. 26.

DETAILED DESCRIPTION

Referring to the Figures, an expandable vertebral implant 20 may provide a variety of support within the spine. The implant 20 may provide support in a space remaining after removal of at least part of a vertebra. In some implementations, the implant 20 may be placed between or be in engagement with a first and second vertebrae.

Figure 2:
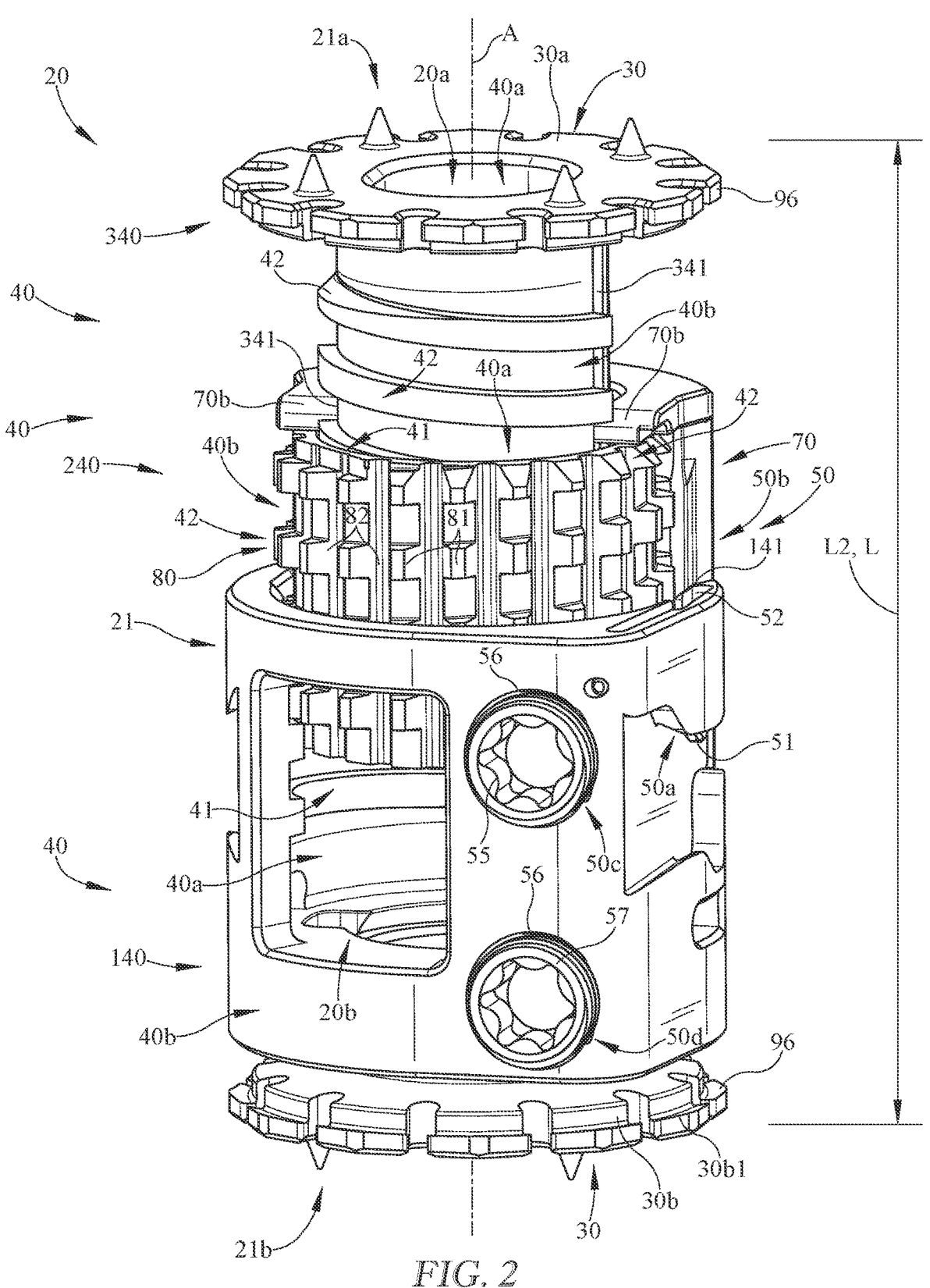
FIG. 2 is a perspective view of the implant of FIG. 1 illustrating the implant occupying a second length larger than the first length.
Figure 3:
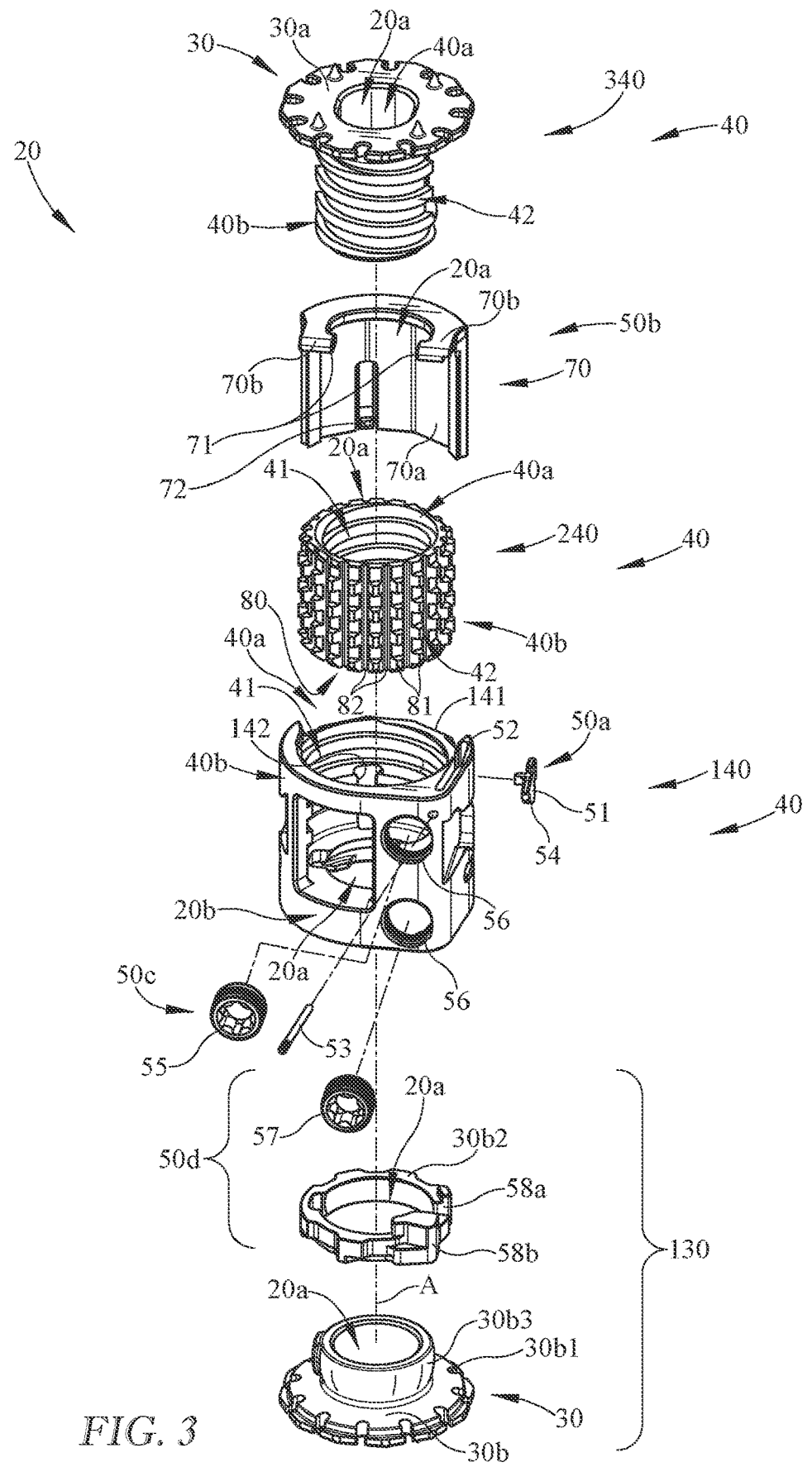
FIG. 3 is an exploded view of the spinal implant of FIG. 1.

The implant 20 may be expandable between a variety of lengths or body lengths L along a longitudinal axis A of the implant 20. The implant may expand and/or collapse between a first length L1 (see FIGS. 1 and 26) and a second length L2 (see FIGS. 2 and 27), wherein the second length is larger than the first length. A body 21 of the implant 20 may include opposing ends. The opposing ends (e.g. first end 21*a* and second end 21*b*) of the implant 20 may move relative to each other along the longitudinal axis A to vary the body length L. One or more ends 21*a, b* (e.g. superior and/or inferior ends) of the implant may include an endplate 30 to engage a portion of the spine or tissue (e.g. first vertebral body, second vertebral body). In some implementations, the endplates 30 may be static/fixed 30*a* and/or adjustable 30*b*. In the embodiment shown, the adjustable endplate 30*b* is polyaxially adjustable. In the embodiment shown, one end 21*a* may include the static endplate 30*a* and the other opposing endplate may be an adjustable polyaxial endplate 30*b* on the other end 21*b*. In some embodiments, one or more of the endplates 30 may include a modular endplate 230 assembled or attached to the endplates 30 of the implant. The implant 20 may include one or more locking mechanisms 50. For example, at least one locking mechanism 50*a*, 150*a*, 50*c* may be used to fix the implant in one or more lengths L. In various embodiments, at least one locking mechanism 50*c* may be used to fix the orientation of the adjustable polyaxial endplate 30*b*, if used. Further, the implant 20, or portions thereof, may include one or more hollow or through openings 20*a*, 20*b* therein to receive graft material. Placement of the autograft or allogenic bone graft material may include cancellous and/or corticocancellous bone graft as an adjunct to fusion. For example, an axial center, canal, core, or through opening 20*a* of the implant (e.g. inner core, middle core, and outer core) may receive the graft material. One or more through openings 20*a* may extend from the first end 21*a* towards the second end 21*b* of the implant 20 (e.g. inner, middle, and/or outer core), or portions thereof. The periphery (e.g. interior and/or exterior) of the implant or portions thereof (e.g. outer core, outer periphery window(s) 20*b*, radial openings) may receive graft material after expansion.

In some implementations, the implant 20 or implant body 21 may include a plurality of members, cylinders, or cores 40 rotating and/or translating relative to each other to expand and/or collapse between one or more body lengths L. The expandable spinal implant 20 may accommodate different surgical approaches (e.g. via inserter tool 60) corresponding to the differing heights of the corpectomy defect, and/or variations in patient anatomy. As shown in the embodiment, the cores 40 (e.g. middle 240, outer 140, and/or inner 340) may be a hollow cylinder having an inner periphery or cylindrical surface 40*a* and/or outer periphery or cylindrical surface 40*b*. Although the embodiment in the Figures illustrates the body 21 having three members, it should be understood that various embodiments of the implant may have two or more cores or members 40 (e.g. two, three, four, etc.) allowing the body length L of the expandable body to be adjusted. The implant 20 or body 21 may be configured to expand from the first end 21*a* to the second end 21*b* along the longitudinal axis A of the body. In some embodiments, the implant 20 or body 21 may include an outer core 140, a middle/rotatable core 240, and/or an inner core 340. The implant/body (e.g. middle core, outer core, and/or inner core), or portions thereof, may be movable and/or threadedly coupled relative to each other. The outer core 140 (e.g. inner periphery) may receive (e.g. telescopically) the middle core 240 and/or the inner core 340. The middle core 240 (e.g. inner periphery) may receive (e.g. telescopically) the inner core 340. When expanding/collapsing between a collapsed position as shown in FIGS. 1, 9, 26, and 29 (e.g. first length L1) and an expanded position as shown in FIGS. 2, 10, 27, and 30 (e.g. second length L2), the middle core 240 rotates and translates along the longitudinal axis A (e.g. relative to the outer core 140 and/or inner core 340) to adjust the location of the outer core 140 relative to the inner core 340 and/or endplates 30, thereby adjusting the body length L of the implant/body. Further, in some embodiments, the inner core 340 may translate relative to the middle core 240 and the outer core 140. A connecting sleeve or follower 70, if used, may rotationally fix the inner core 340 relative to the outer core 140 during length adjustment between the collapsed position and the expanded position. The connecting sleeve 70 may translate along the longitudinal axis A between the collapsed position (see FIGS. 9 and 29) and the expanded position (see FIGS. 10 and 30). Further, the connecting sleeve 70 may translate with the middle core 240 relative to the outer core 140 and/or inner core 340. The outer core 140 and the inner core 340 may be keyed rotationally by the connecting sleeve 70 for retention, to prevent relative rotation therebetween, and/or allowing translation along the longitudinal axis A. Although the sleeve is shown in the Figures, the sleeve may be a variety of shapes, sizes, quantities, and construction and still be within the scope of the invention. For example, the sleeve/structure/member 70 may be one or more internal/external members that engage the outer core and the inner core and does not allow rotation of the inner core relative to the outer core.

In some implementations as shown in FIGS. 1-3, 10-13, 26-28, and 30-32, the implant 20, body 21, and/or one or more cores 40 may include one or more threads, helical engagement structure, or threaded engagement to expand and/or collapse the body between one or more body lengths L. The cores 40 (e.g. middle 240, outer 140, and/or inner 340) may include internal threads 41 and/or external threads 42 so that axial rotation of one or more cores 40 will result in axial displacement of one or more cores 40. As shown in the Figures, the middle core 240 may include external or first threads 42 on the external periphery 40*b* and internal or second threads 41 on the internal periphery 40*a*. The inner core 340 may include external or third threads 42 on the external periphery 40*b*. The outer core 140 may include internal or fourth threads 41 on the internal periphery 40*a*. The middle core 240 may be threadedly coupled to both the outer core 140 and the inner core 340. The outer core 140 may be threadedly coupled to the middle core 240. The inner core 340 may be threadedly coupled to the middle core 240.

The first threads 42 of the middle core 240 may be different (e.g. different directions, clockwise, counterclockwise, pitch, quantity, size, shape, etc.) from the second threads 41 of the middle core. The threads 41, 42 of the middle core 240 may run or be threaded in opposite directions. For example, the first threads 42 may be right hand threads of the middle core 240 and the second threads 41 may be left hand threads of the middle core 240. As shown in the Figures, the hollow threaded interior portion 40*a* of the outer core 140 may be configured to receive the middle core 240 and the inner core 340 therein. The hollow threaded interior portion 40*a* of the middle core 240 may be coaxially configured to receive the inner core 340 therein and a threaded external portion 40*b* may be configured to engage the hollow interior portion 40*a* of the outer core 140. The threads, helical engagement structure, or thread engagements may be a variety of shapes, sizes, quantities, and constructions and still be within the scope of the invention. For example, the one or more threads may be a helical ramp. The one or more threads of the core(s) 40 may have different characteristics and/or constructions.

In some implementations, the middle core 240 may be rotated relative to the outer core 140 to axially displace both the middle core 240, the inner core 340, and sleeve 70. The middle core 240 (e.g. outer periphery or surface 40*b*) may include a gear mechanism 80 or a plurality of gear teeth 81 and/or recesses 82 about the periphery 40*b* of the middle core 240. As shown in the embodiment, the plurality of gear teeth 81 and/or recesses 82 are in a helical pattern. For example, the first thread 42 of the middle core 240 (e.g. outer periphery 40*b*) may be or include the gear teeth 81 and/or recesses 82. The first thread 42, recesses 82, and/or gear teeth 81 engage the internal threads 41 of the outer core 140 and/or tool 60 (e.g. inserter). The recesses 82 may be cut or below a portion (e.g. threads, between the teeth) of the middle core outer periphery 40*b*. An inserter or implant tool 60 may engage one or more teeth 81 and/or recesses 82 through an outer peripheral opening or window 20*b* of the outer core 140 with corresponding structure (e.g. gear mechanism 68, one or more gear teeth or recesses) to axially rotate the middle core 240 relative to the outer core 140 and/or inner core 340. The spinal implant 20 may be positioned within the patient's spine with the inserter 60 carrying the implant 20. Rotating the middle core 240 via the inserter may cause the spinal implant to expand/collapse from the first length L1 to the second length L2.

Figure 4:
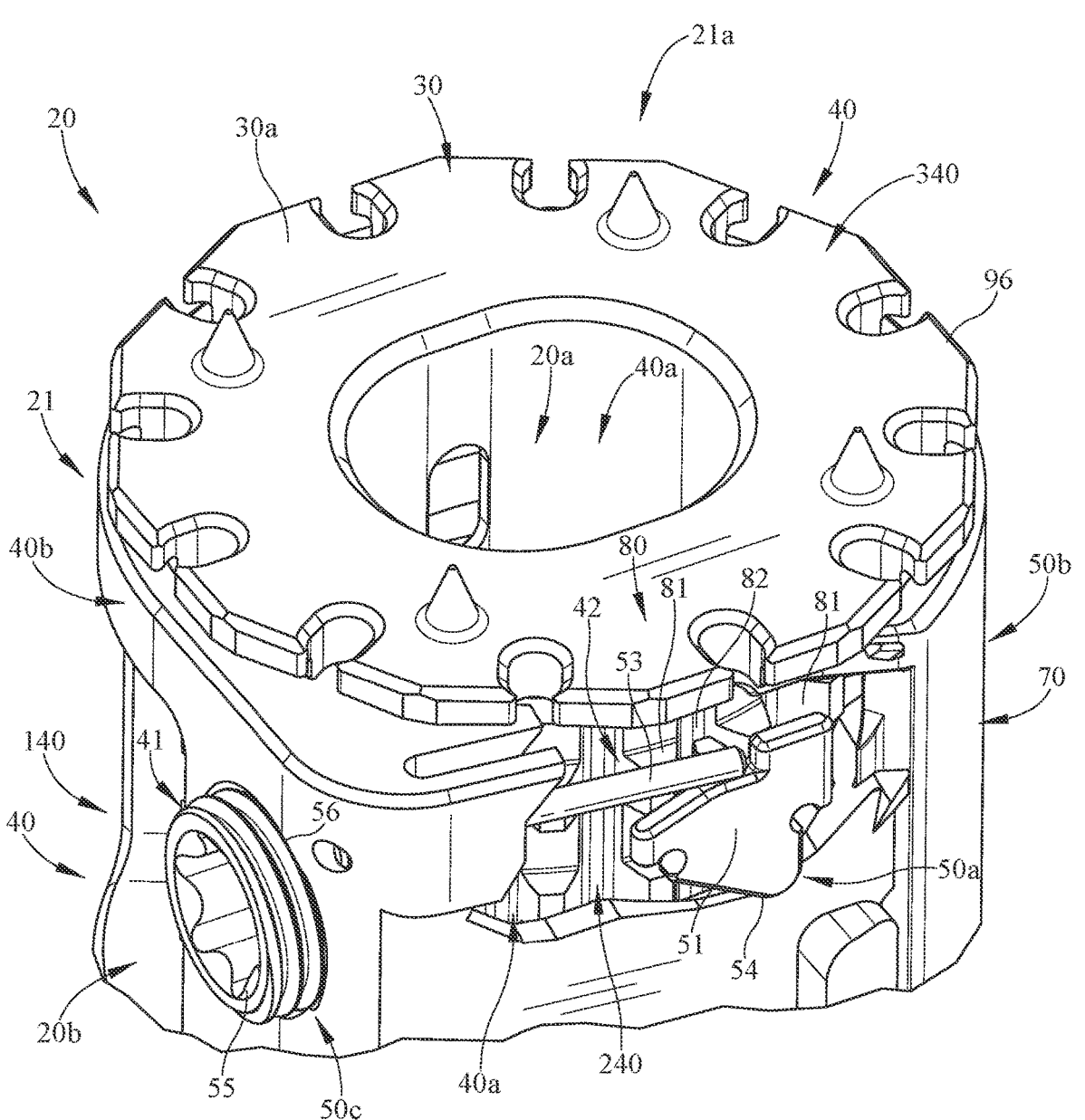
FIG. 4 is perspective view of the implant of FIG. 1 illustrating an embodiment of a first locking mechanism in a locked state.
Figure 5:
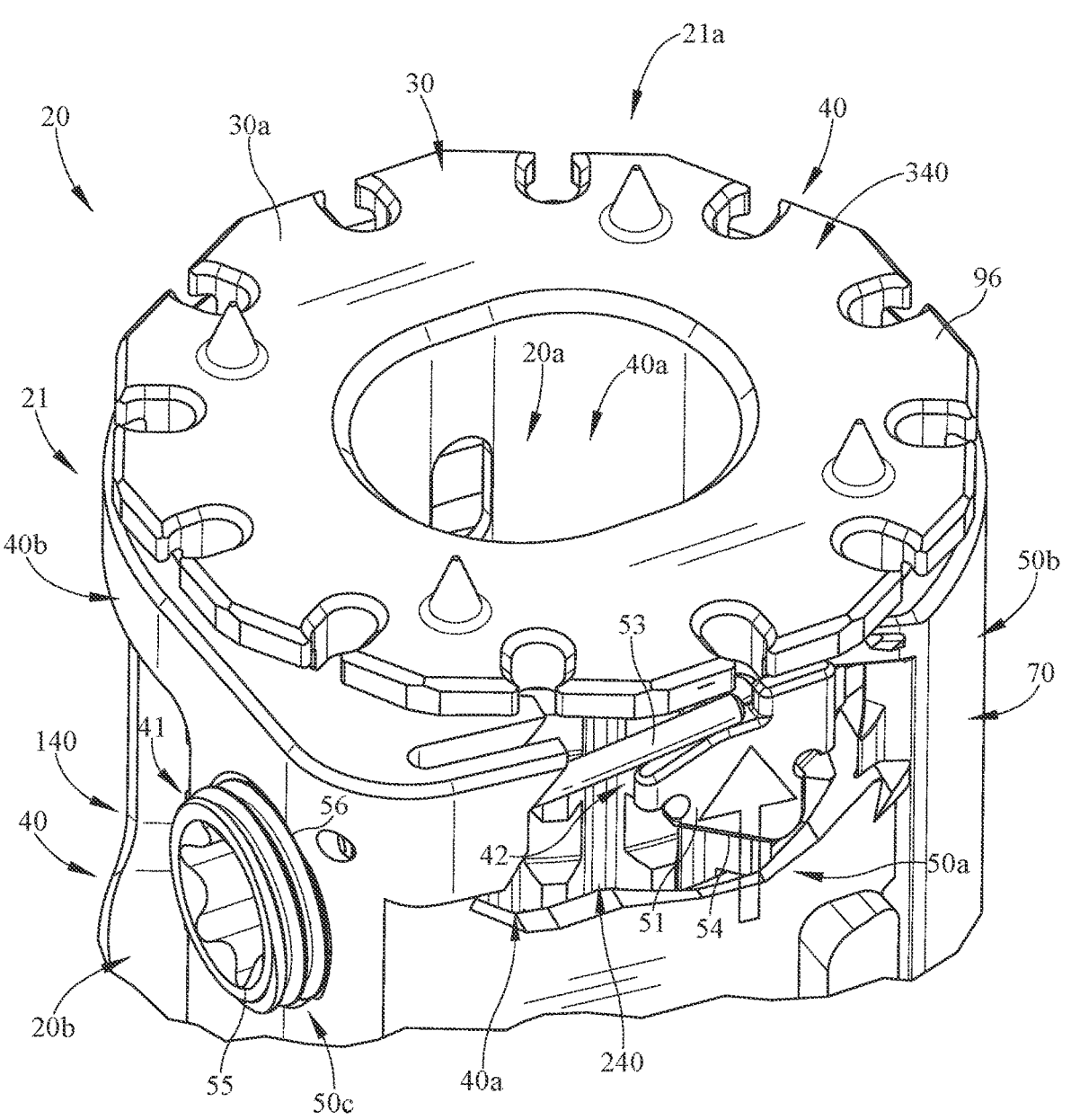
FIG. 5 is perspective view of the implant of FIG. 4 illustrating an embodiment of the first locking mechanism in an unlocked state.

In some implementations, the implant 20 may include one or more locking mechanisms 50. One or more locking mechanisms 50*a*, 150*a*, 50*c*, 50*b*, 70 may engage the outer core 140 with the middle core 240 and/or inner core 340. The one or more locking mechanisms (e.g. 50*a*, 150*a*, 50*b*, connecting sleeve 70) may be configured to translate along the longitudinal axis A. Although the translation along the longitudinal axis is shown in the one embodiment in the Figures, the one or more locking mechanisms may translate/move/rotate/pivot in one or more directions along one or more axes in some embodiments. A first locking mechanism 50*a*, 150*a* may lock the axial and/or rotational displacement of the implant 20/body 21, or portions thereof. The first locking mechanism may be configured to releasably lock the length L of the body. The first locking mechanism 50*a*, 150*a* may be dynamically coupled or engage the outer core 140. The first locking mechanism 50*a*, 150*a* may include one or more engagement members or locking members 51 (e.g. one or more teeth and/or recesses) protruding medially towards the longitudinal axis A or from the outer core 140 towards the middle core 240. Although the engagement members or locking members 51 protrude medially towards the longitudinal axis A as shown in the one embodiment of the Figures, members 51 may project in one or more directions along one or more axes. In some embodiments, the engagement member 51 may be in a helical shape or pattern. The first locking member 50*a*, 150*a* may be configured between a locked state (see FIGS. 4 and 6) and an unlocked state (see FIGS. 5 and 7). When in the locked state, the first locking mechanism 50*a*, 150*a* or engagement member 51 engages with one or more of the gear mechanisms 80 (e.g. gear teeth 81 and/or recesses 82) of the middle core 240, thereby fixing the body length L and/or the middle core 240/inner core 340 relative to the outer member. When in the unlocked state, the first locking mechanism 50*a* or engagement member 51 may be disengaged with one or more of the gear teeth 81 and/or recesses 82 of the middle core 240, thereby allowing the body length L to be adjusted and/or allowing the middle core 240/inner core 340 to rotate and/or translate relative to the outer member. The engagement member 51 may be positioned within the recess 82 between the teeth 81/thread 42 making up the middle core threads 42 and/or positioned between the threads 42 of the outer core 140 when in the locked state thereby blocking/obstructing the middle core threads 42 from traveling with/between the threads 41 of the outer core 140. The engagement member 51 may be positioned out of the recess 82 between the teeth 81/thread 42 making up the middle core threads 42 and/or positioned in line with the threads 42 of the outer core 140 when in the unlocked state thereby unblocking/unobstructing the middle core threads from traveling with/between the threads 41 of the outer core 140. The locking mechanism 50*a*, 150*a*, 50*b*, 70 (e.g. first, second, etc.) may translate along the longitudinal axis A. The engagement member 51 may travel in a linear slot 52 in the axial direction in some embodiments. In some implementations, the first locking mechanism 50*a*, 150*a* may include one or more biasing members or a biased locking member 53. The one or more biasing members 53 may urge the first locking mechanism 50*a*, 150*a* and engagement member 51 towards the locked state to fix the rotation of the middle core 240 and/or inner core 340 relative to the outer core 140. As shown at least in FIGS. 5 and 7, the biasing member(s) 53 may urge the engagement member 51 towards one or more of the plurality of gear teeth 81 and/or recesses 82 of the middle core 240. The engagement member 51 may have a cam 54 (e.g. lower end) that engages a cam guide 64 of the inserter or tool 60 to drive the first locking mechanism 50*a*, 150*a* or engagement member 51 away from the locked state towards the unlocked state to allow the middle core 240 to rotate and the body length L to be adjusted.

One embodiment of the first locking mechanism 50*a* is shown in FIGS. 1-5, 8-16, 19-22, 26-32. The engagement member 51 includes one or more biasing members 53 separate therefrom or non-integral. An opening or the slot 52 may receive the biasing member 53. The biasing member 53 is a leaf spring biasing the engagement member 51 towards the locked state. The biasing member may be a variety of shapes, sizes, quantities, and constructions and still be within the scope of the invention. Although a leaf spring is shown in the one embodiment, a variety of springs may be used. For example, a torsion, tension, spiral, and/or compression spring may be used in some embodiments.

Figure 6:
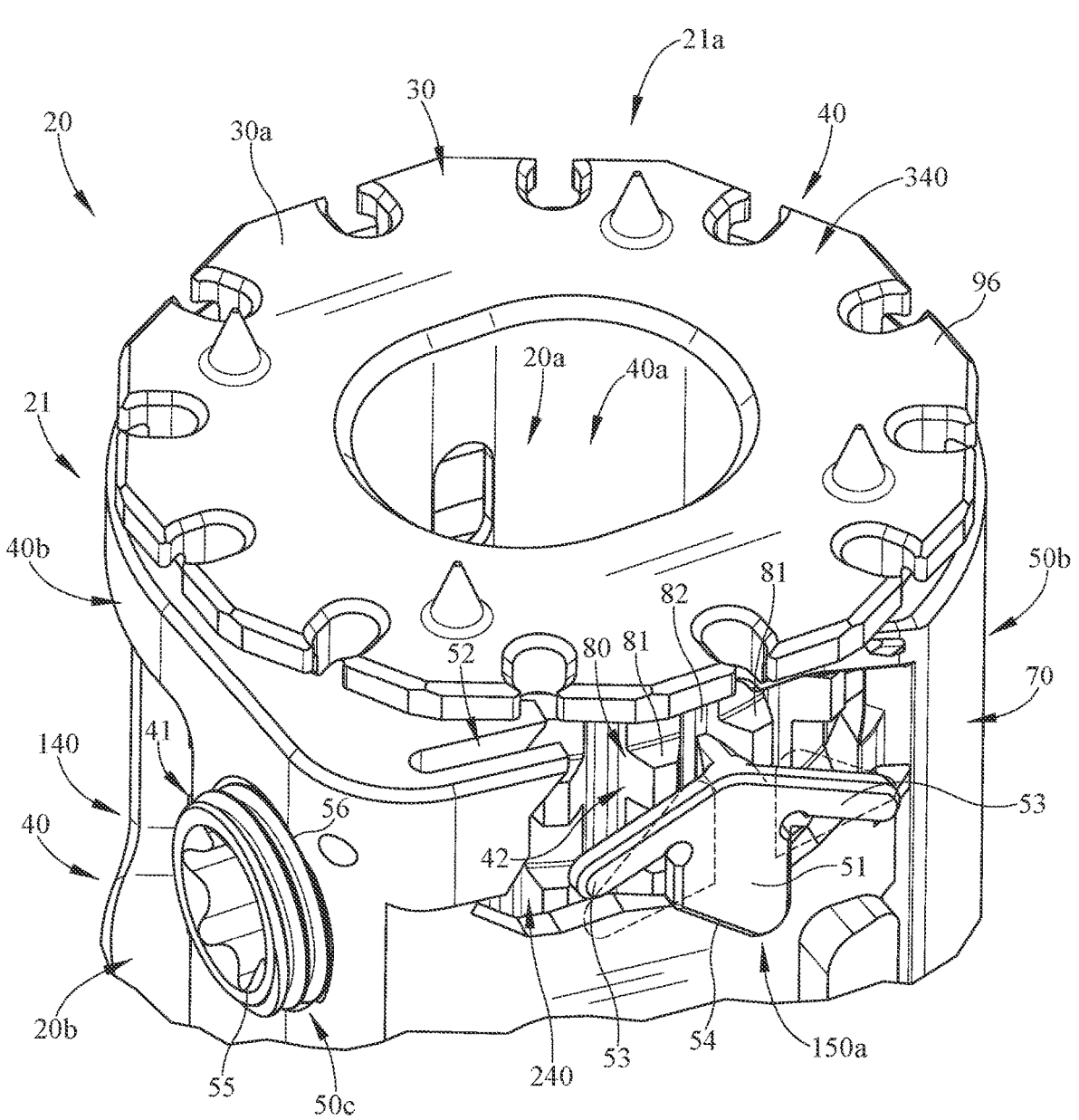
FIG. 6 is perspective view of the implant of FIG. 1 illustrating another embodiment of a first locking mechanism in a locked state.
Figure 7:
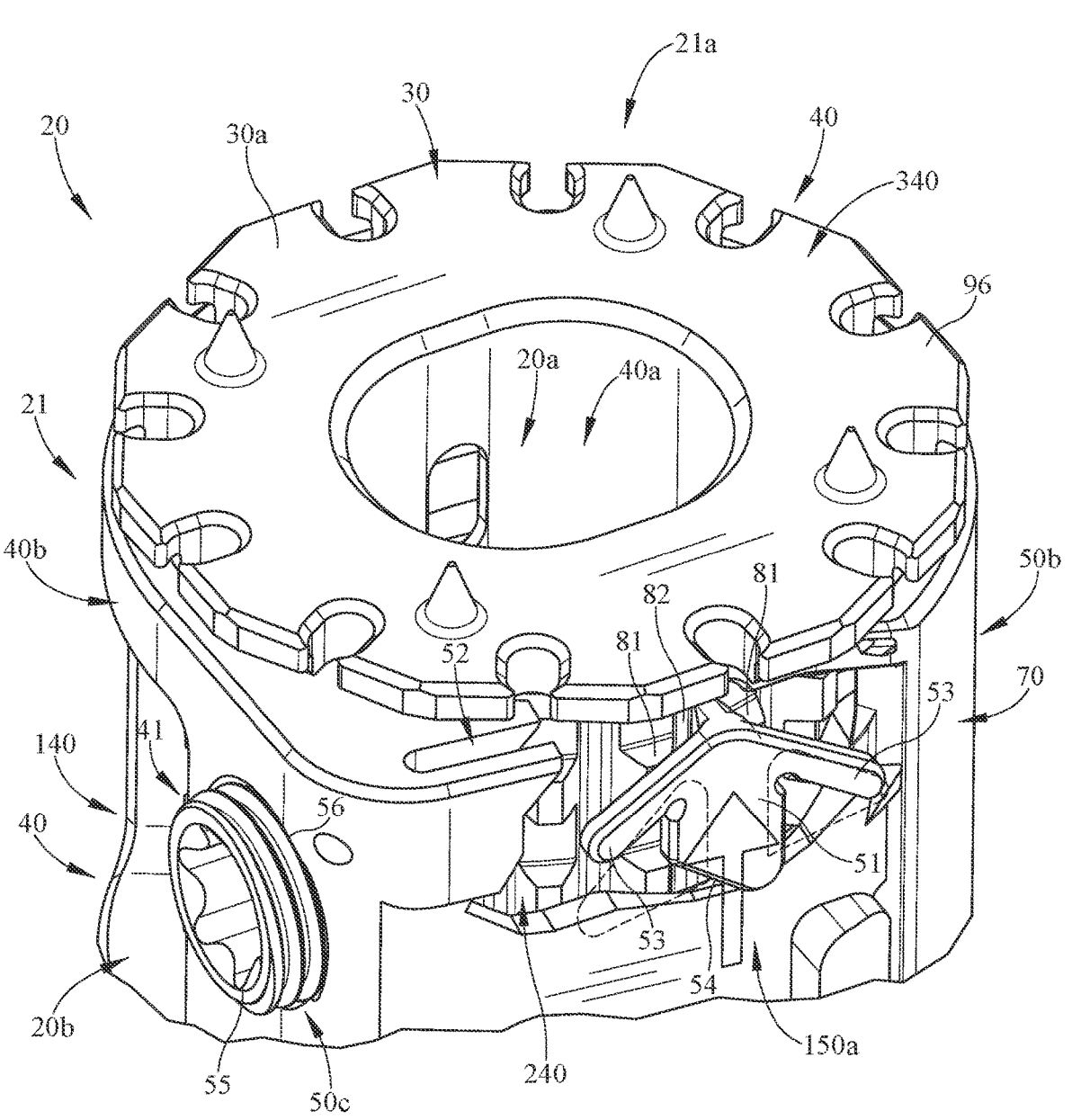
FIG. 7 is perspective view of the implant of FIG. 6 illustrating an embodiment of the first locking mechanism in an unlocked state.

Another embodiment of the first locking mechanism 150*a* is shown in FIGS. 6 and 7. The engagement member 51 includes one or more biasing members 53 combined or integral with the engagement member. The biasing member 53 may be a leaf spring extending/projecting from one or more sides of the engagement member biasing the engagement member towards the locked state. The engagement member 51 is arrow-shaped with the leaf springs extending downwardly and away from the member on opposing lateral sides.

In some implementations, another locking mechanism 50, 50*b* may rotationally fix or secure the outer core 140 and the inner core 340 together. One or more second locking mechanisms 50*b* may engage the outer core 140 with the inner core 340, thereby locking the rotation about the longitudinal axis A of the inner core 340 relative to the outer core 140. The connecting sleeve 70 may be the second locking mechanism 50*b*. The connecting sleeve 70, if used, translates with the middle core 240 when expanding and/or collapsing the implant. As shown in FIGS. 9, 10, 29, and 30, the connecting sleeve 70 translates relative to the inner core 340 and/or the outer core 140 when expanding and/or collapsing the implant 20. A first portion 70*a* of the connecting sleeve 70 axially translates within and/or is received within an axial groove or slot 141 within the outer periphery 40*b* of the outer core 140. The lateral/opposing sides of the sleeve first portion 70*a* may include a dovetail engagement with the one or more sides of the axial groove 141 of the outer core 140 as shown in the one embodiment in the Figures. The first portion 70*a* or sleeve 70 may include a pin and slot engagement, if used, between the sleeve 70 and the outer core 140. In the one embodiment shown in FIGS. 3 and 12, a pin 72 (e.g. spring loaded and/or hinged tab/pin/clip) of the sleeve 70 may axially translate within and/or is received within an axial groove or slot 142 within the outer periphery 40*b* of the outer core 140. In the one embodiment shown in FIGS. 28 and 32, a pin 72 (e.g. cylindrical pin, projecting inwardly from the first portion) of the sleeve 70 may axially translate within and/or is received within an axial groove or slot 142 within the outer periphery 40*b* of the outer core 140. A second portion 70*b* (e.g. arms, pair of arms with inwardly projecting pins 71) of the connecting sleeve 70 axially translates within and/or is received within one or more axial grooves or slots 341 within the outer periphery 40*b* of the inner core 340. As shown in the one embodiment in FIGS. 1-15, 19-22, 24, and 25, the connecting sleeve 70 or second portion 70*b* may be an arcuate member with opposing free ends/arms/pins 71 defining the through opening 20*a*, projecting inwardly, and/or dynamically engaging the slots 341 of the inner core 340. As shown in the one embodiment in FIGS. 26-32, the connecting sleeve 70 or second portion 70*b* may be a fully enclosed ring and/or inwardly projecting pins 71 defining the through opening 20*a*, projecting inwardly, and/or dynamically engaging the slots 341 of the inner core 340. The connecting sleeve 70 or second locking mechanism 50*b* rotationally locks the outer core 140 with the inner core 340 while allowing the inner core and/or middle core to translate relative to each other and/or the connecting sleeve.

Figure 8:
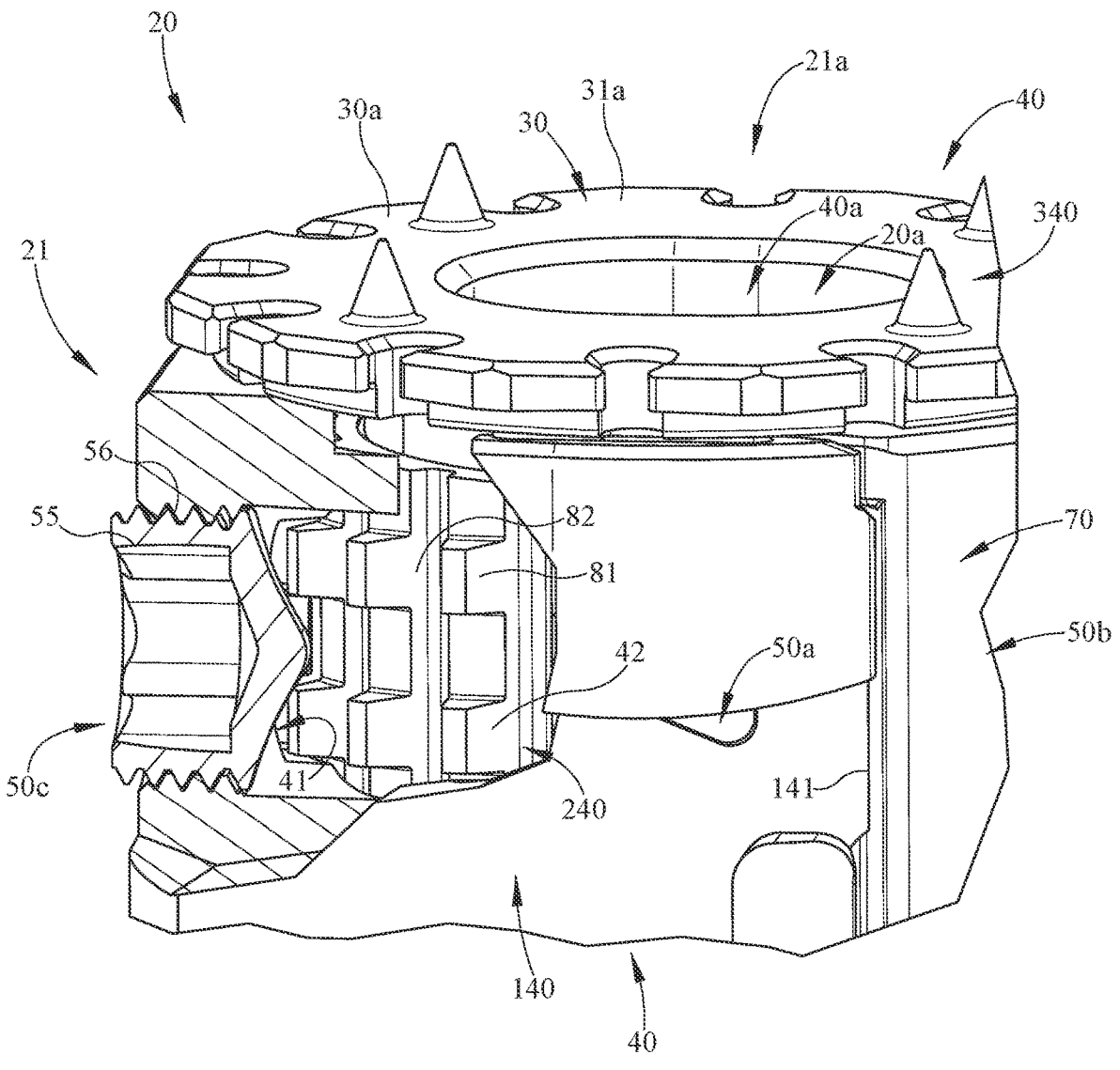
FIG. 8 is perspective view of the implant of FIG. 1 illustrating an embodiment of a second locking mechanism in a locked state.
Figure 9:
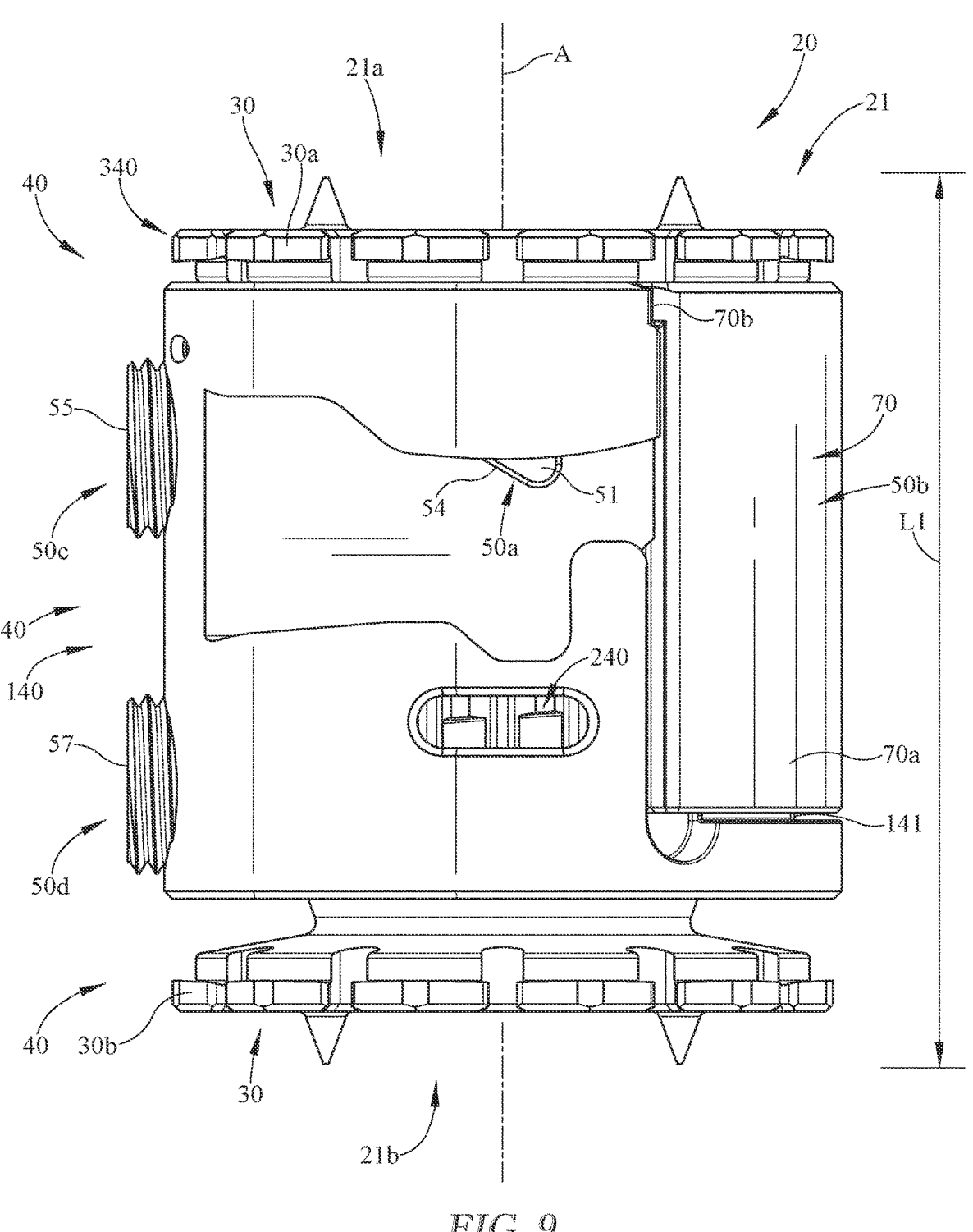
FIG. 9 is side view of the implant of FIG. 1 illustrating the implant in the first length.
Figure 10:
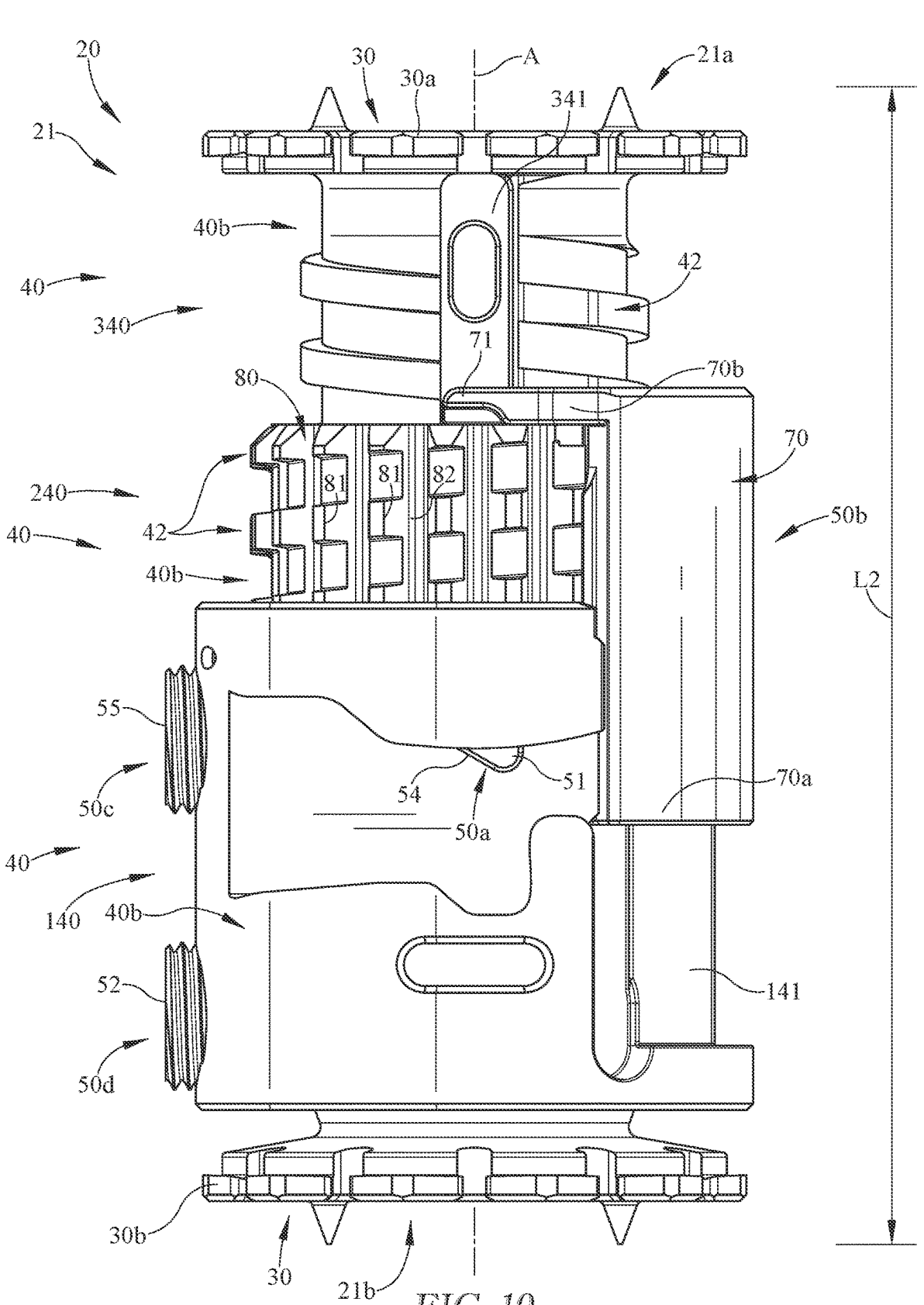
FIG. 10 is side view of the implant of FIG. 2 illustrating the implant in the second length.
Figure 11:
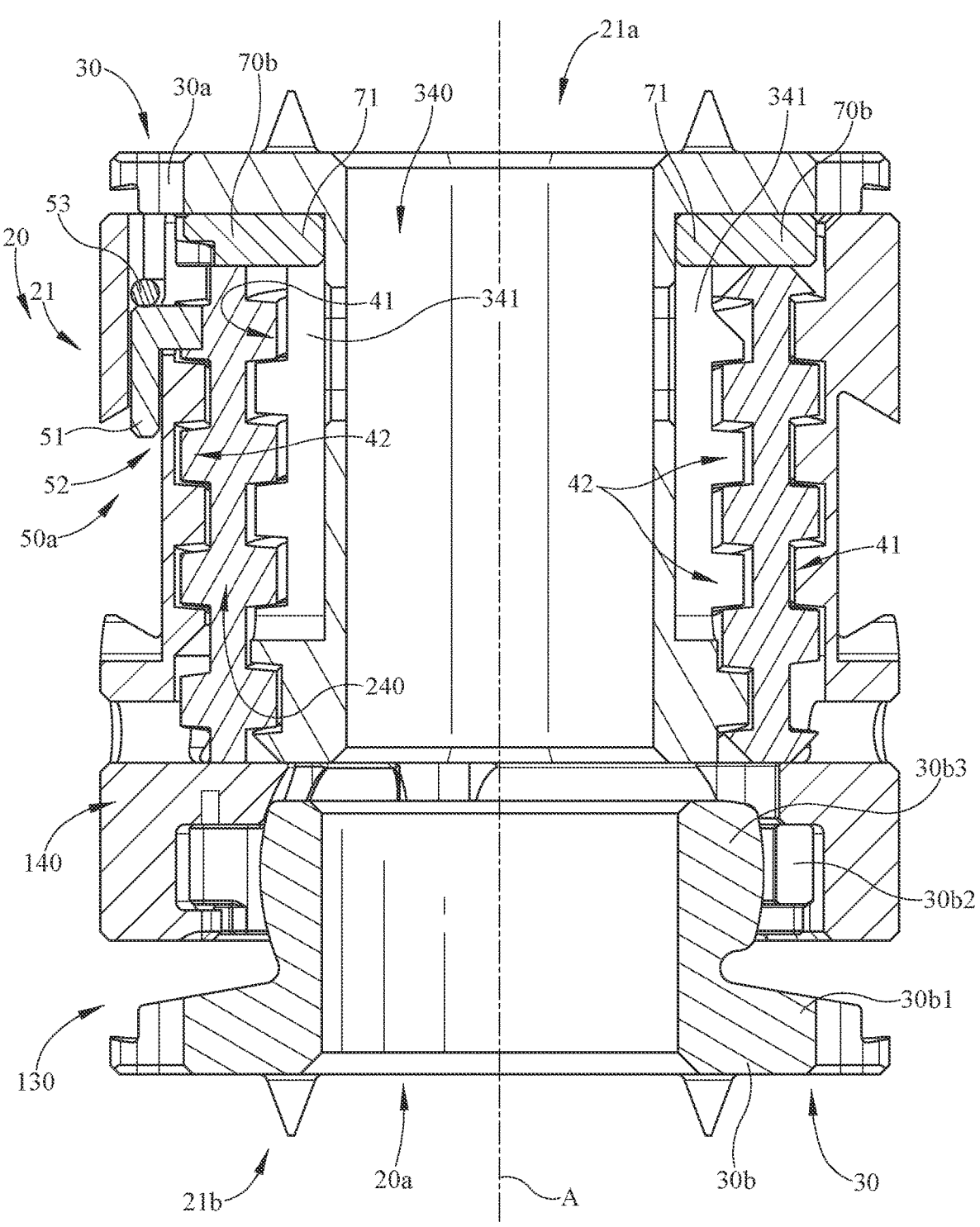
FIG. 11 is a sectional view of the implant of FIG. 1 taken along line 11-11.
Figure 12:
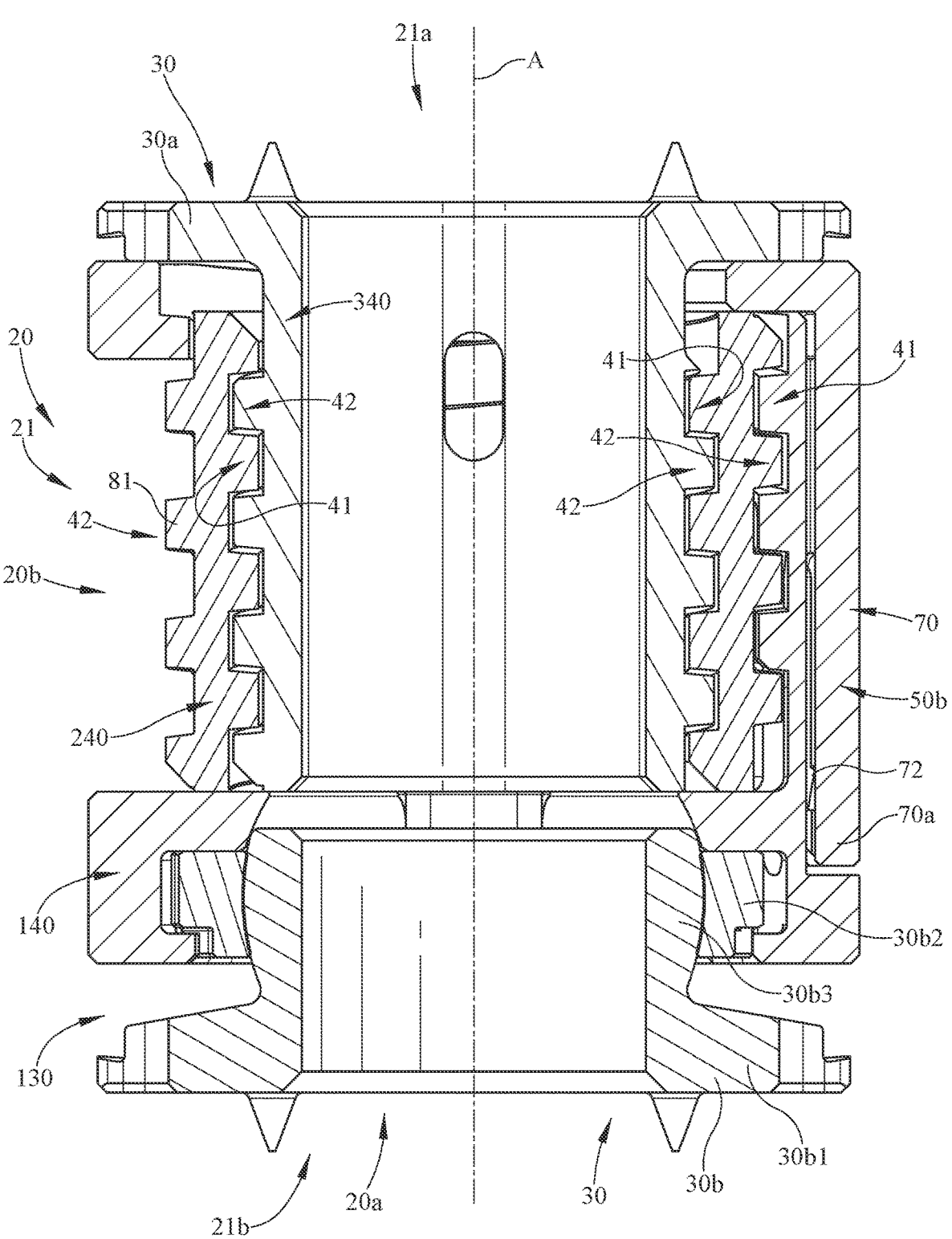
FIG. 12 is a sectional view of the implant of FIG. 1 taken along line 12-12.
Figure 13:
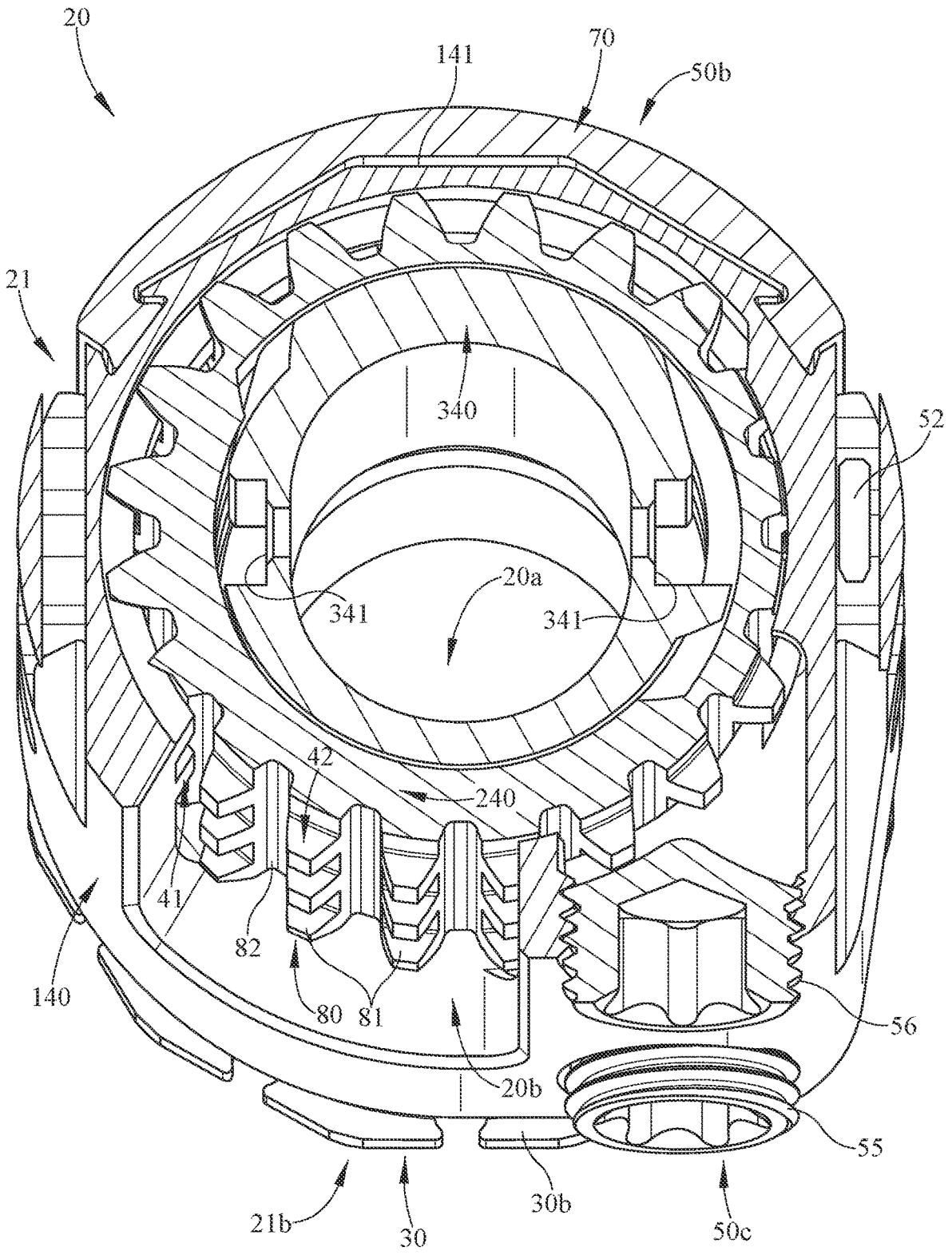
FIG. 13 is a sectional view of the implant of FIG. 1 taken along line 13-13.
Figure 14:
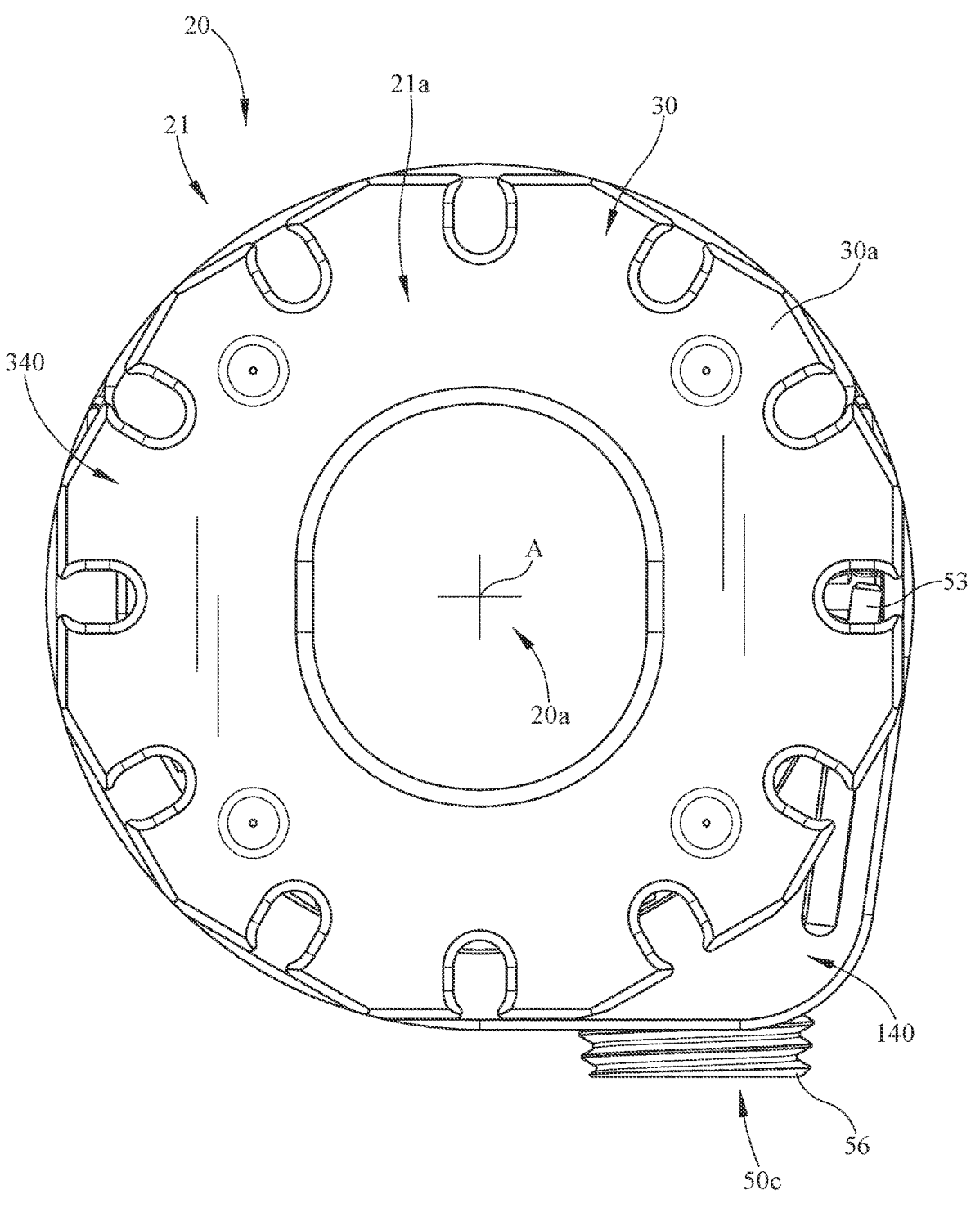
FIG. 14 is a top view of the implant of FIG. 1.

In some implementations as shown in FIGS. 8 and 13, another locking mechanism 50, 50*c* may be used to lock the middle core 240 and the outer core 140 from rotating relative to each other. A third locking mechanism 50*c*, if used, may be a first set screw 55 coupling the outer core 140 with the middle core 240 to fix rotation and/or axial movement. A counter bore or through hole 56 (e.g. threaded) extends from the outer surface or periphery 40*b* of the outer core 140 to the inner surface or periphery 40*a* of the outer core 140. The first set screw 55 threadedly engages the through hole 56 and engages the middle core 240 in a locked state (see FIG. 8) and disengages the middle core 240 in the unlocked state (see FIGS. 1 and 26). In the locked state, the middle core 240 may not rotate and/or travel axially relative to the outer core 140. In the unlocked state, the middle core 240 may rotate and/or travel axially relative to the outer core 140. The bore or set screw direction/orientation (e.g. axis) may not intersect or may be offset away from the longitudinal axis.

In some embodiments as shown in FIGS. 11, 12, 15, 16, 31, and 32, one or more endplates 30 may be an adjustable polyaxial or articulatable plate 30b or articulatable endplate assembly 130. The articulatable endplate assembly 130, if used, may include an articulatable plate 30b, flexible collar 30b2, and/or one or more locking members 57 (e.g. a second set screw). As shown in FIG. 15, the angulation θ of the articulatable endplate or assembly may be variable within a cone of 20 degrees (+/−10 degrees). A variety of angulation θ may be used and still be within the scope of the invention. For example, a cone of 20 degrees (+/−5 degrees) may be used. For example, a cone of 10 degrees (+/−5 degrees) may be used. For another example, a cone of 30 degrees (+/−5 or +/−10 degrees) may be used. The implant may facilitate two distinct degrees of freedom to allow articulation of the body 30b3 (e.g. rounded) relative to the first end 21a and/or second end 21b. The polyaxial endplate assembly 130, if used, may be adjusted and/or locked before or after implantation to either prescribe additional lordosis/kyphosis to the implant construct, allow the endplate to self-adjust, and/or conform to the corresponding contact surface of the vertebral body during expansion. The polyaxial endplate assembly 130 or adjustable endplate 30 may be attached to the one or more ends 21a, 21b of the implant (e.g. first end, second end, inner core, outer core). The polyaxial endplate 30b or assembly 130 may pivot along at least two intersecting axes disposed in the same plane that is not parallel to the longitudinal axis. The articulatable plate 30b may include the endplate or member 30b1 and a rounded body 30b3. The endplate 30b1 may include a top wall, wherein the top or contacting wall may include a substantially planar surface orientated transverse to the longitudinal axis and movable relative to an orientation of a vertebra or tissue. The clamping assembly may be disposed circumferentially around and/or over the body of the articulatable plate. Although not shown, the rounded body 30b3 may include a plurality of steps, grooves, and/or other textures (e.g. first steps). Further, the flexible collar or member 30b2 may include a plurality of steps, grooves, and/or other textures (e.g. second steps) dynamically coupled to the steps of the rounded body 30b3, if used. The rounded body may include a spherical surface as shown in the embodiment. In some implementations, the implant 20 and/or articulatable plate 30b may include a clamping assembly or locking mechanism 50d that may include the collar clamp 30b2 around the rounded body 30b3 (e.g. spherical head) of the endplate 30b1 coupled with the locking member 57 (e.g. second set screw). The clamping assembly 50d may include the collar 30b2 having one fixed end 58a fixed relative to the clamping assembly and one free end 58b and the locking member 57 (e.g. second set screw). Although the locking member 57 is shown as a second set screw in the one embodiment, the locking member may be a variety of quantities, shapes, sizes, constructions, structures and/or devices and still be within the scope of the invention. For example, the locking member may be a cam, ratchet, etc. The second set screw 57, if used, may be threadedly received within the counterbore 56 within the clamping assembly or outer core 140. The locking member or second set screw 57 may be configured to press against the free end 58b of the flexible collar or member 30b2 thereby applying radial compression to at least a portion of the body 30b3 of the articulatable plate 30b, thereby fixing the endplate 30b1 with respect to the clamping assembly and/or implant, or portions thereof. The flexible collar 30b2 may extend around the rounded body 30b3, or portion thereof. The collar clamp 30b2 may be flexible. Rotation of the locking member or set screw 57 closes the collar clamp 30b2, increasing the clamping force on the spherical head 30b3 of the endplate and locking the articulatable endplate (e.g. endplate, body) in place so that it cannot rotate/pivot or move out of position. The locking member or second set screw 57 may be dynamically coupled with the collar and configured to apply a radial compression to at least a portion of the circumference of the articulatable plate/body, thereby fixing the articulatable plate with respect to the body/assembly and/or core (e.g. outer, middle, inner). The locking member/second set screw 57 and/or bore 56 may be offset away from or at a radial distance from the longitudinal axis. The fixed plate 30a, if used, may be on the other end 21a of the implant not attached with the polyaxial endplate assembly. Both the polyaxial and static integrated endplates may have spikes to resist migration of the implant, and attachment features 90, if any, to allow the optional attachment of a modular endplate 230.

In some implementations as shown in FIGS. 22-33, the implant 20 may include one or more modular endplates 230 attached to one or more endplates 30a, 30b. The modular endplates 230, if used, may include a variety of footprints and lordotic/kyphotic angles to accommodate patient-specific anatomy and the correction desired. The modular endplates may be different in size, shape, and construction to each other and/or than the endplates 30a, 30b attached thereto. The modular endplate 230 may be attached to the one or more ends of the implant (e.g. first end, second end, static endplate, polyaxial endplate). Spikes on the vertebral-body-facing-surface of the modular endplates may be designed to resist migration of the core; other similar vertebral-engaging structures may also be employed in addition to, or in place of, such spikes. The endplates and/or modular endplates, or portions thereof, may include an attachment mechanism 90. The attachment mechanism 90 may be included in the first end 21a and/or second end 21b of the implant. One embodiment of the attachment mechanism 90 is shown in FIGS. 22-25, the modular endplates 230 may include two or more hooks 91 positioned on opposite sides of the inner bore of the modular endplate 230. One or more hook(s) 91a may be static and/or the other hook(s) 91b may be flexible/dynamic. The attachment mechanism 90 may include a cam mechanism or cam (e.g. lip 96, endplate) to flex/urge the one or more hooks 91 of the modular endplate 230, or portions thereof, into engagement with the integrated implant 30a, 30b. To attach the modular endplate 230 to the implant 20 (e.g. core, endplate, static endplate, and/or polyaxial endplate), as shown in FIG. 24 the static hook 91a may be first hooked under a lip 96 or attachment mechanism 90 of the integrated endplate on the implant. As shown in FIG. 25, then the modular endplate 230 may be rotated down so that the flexible hook 91b cams/flexes outward around the lip and then snaps under the opposite lip of the integrated endplate, securing the modular endplate to the core. Although not shown, a snap ring may be positioned within the inner bore of the modular endplate to lock into an annular groove in the outer diameter of the endplate and/or core, securing the modular endplate to the core (e.g. inner core, outer core, etc.).

Another embodiment of the attachment mechanism 90 is shown in FIGS. 26-33, the modular endplates 230, or portions thereof, may include a threaded engagement with the one or more endplates 30a, 30b, or portions thereof. The modular endplate 230, threaded engagement, and/or attachment mechanism 90, if used, may include one or more screws 92 (e.g. set screw) threadedly engaging the modular endplate 230 to the endplate 30a, 30b. In the one embodiment shown in FIGS. 26-33, the inner periphery 40a or through opening 20a of the endplates 30a, 30b may include one or more threads (e.g. female) to engage the modular endplate (e.g. screw 92, male threads). In some embodiments, the screw 92 may include a through opening 93. The through opening 93 of the screw may receive or position a material, such as but is not limited to bone graft material. A through opening 20a of the modular endplate may receive the screw 92 therethrough to engage the inner periphery 40a or threads of the one or more endplates 30a, 30b. A larger head or flange 92a of the screw 92 may engage a recess/ ledge 92b within the though opening 20a of the modular endplate 230. It should be understood that a variety of attachment mechanisms may be used and still be within the scope of the invention. For example in some embodiments, a screw may not be used such that the modular endplate includes an integral threaded portion (e.g. male) to engage the corresponding endplate 30a, 30b.

In some implementations as shown in FIGS. 17-21, the implant 20 may include one or more tools and/or inserters 60. The inserter 60, if used, may releasably couple the implant and/or operably engage the implant (e.g. first set screw, second set screw, locking member, middle core, outer core, locking mechanism(s)). The inserter 60 (e.g. arm(s)) when coupling with the implant (e.g. pair of lateral slots/ receivers in outer periphery of the outer core) moves the first locking mechanism 50a, 150a and/or engagement member 51 from the locked state (see FIG. 19) to the unlocked state (see FIGS. 20 and 21). When the inserter is coupled, the cam 64 or arm(s) may urge the biasing member(s) 53 or engagement member 51 towards the unlocked state. Decoupling the inserter from the implant may move or displace the first locking mechanism 50a, 150a and/or engagement member 51 from the unlocked state to the locked state. The biasing member(s) 53 may urge the engagement member towards the locked state when the inserter is decoupled. The inserter may have one or more engagements 65 (e.g. hex, Allen wrench end, driver) to operably engage the one or more set screws (e.g. first set screw, second set screw, locking member). The inserter may include one or more gears 68 to engage the middle core (e.g. teeth and/or recesses) to rotate the middle core clockwise and/or counterclockwise. The implant/inserter may be used to place/position the implant in a smaller collapsed height and corresponding smaller incision.

Components of the presently described implant and/or inserter may be manufactured of various materials, including clinical grade materials. Example materials include, but are not limited to, carbon fiber, various metals and alloys thereof, including stainless steel, titanium, titanium alloys, aluminum, aluminum alloys, cobalt chromium, molybdenum, molybdenum alloys, nickel, nickel alloys, and/or combinations thereof. Silicone and silicone blends may also be used to fabricate one or more component(s) of the implant and/or inserter device. Further, materials of construction for one or more of the components of the present implant and/or inserter include fluoropolymer and other plastics. Examples include PEEK (polyetheretherketone), PPS (polyphenylene sulfide), PPSU (polyphenylsulfone), FEP (fluorinated ethylene propylene), PCTFE (polychlorotrifluorylethylene), PFA (perfluoroalkoxy), ETFE (ethylene tetrafluoroethylene), ECTFE (ethylene chlorotrifluoroethylene), and the like. Composites and/or combinations thereof of the above or similar materials may also be employed.

In particular, materials of construction employed in one or more components of the presently described implant and/or inserter are able to withstand autoclaving, including parameters such as saturated steam under pressure, (~1 atm), along with concomitant autoclave chamber temperatures ranging from about 100° C. to 150° C. for about 15 to 60 minutes. Other relevant autoclaving and/or sterilization procedures and temperatures may also be employed.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It is to be understood that the embodiments are not limited in its application to the details of construction and the arrangement of components set forth in the description or illustrated in the drawings. The invention is capable of other embodiments and of being practiced or of being carried out in various ways. Unless limited otherwise, the terms "connected," "coupled," "in communication with," and "mounted," and variations thereof herein are used broadly and encompass direct and indirect connections, couplings, and mountings. In addition, the terms "connected" and "coupled" and variations thereof are not restricted to physical or mechanical connections or couplings.

The foregoing description of several embodiments of the invention has been presented for purposes of illustration. It is not intended to be exhaustive or to limit the invention to the precise steps and/or forms disclosed, and obviously many modifications and variations are possible in light of the above teaching.

16

The invention claimed is:

1. A spinal implant comprising:
an expandable body configured to expand from a first end to a second end along a longitudinal axis, the expandable body having an outer core, a middle core, and an inner core threadedly coupled and moveable relative to each other along the longitudinal axis, the middle core configured to simultaneously rotate about and translate along the longitudinal axis within the outer core and to cause the inner core to simultaneously translate along the longitudinal axis with respect to both the middle core and the outer core thereby adjusting a body length of the expandable body; and
wherein:
one or more locking mechanisms coupled to the outer core are configured to physically contact and engage with the middle core, and
the middle core or the outer core is a single-piece monolithic mechanism, the middle core comprises internal threads and external threads, and the outer core comprises internal threads.

2. The spinal implant of claim 1 further comprising a connecting sleeve, wherein the connecting sleeve translates along the longitudinal axis and/or does not allow rotation of the inner core relative to the outer core.

3. The spinal implant of claim 1 wherein the middle core includes a plurality of gear teeth or recesses.

4. The spinal implant of claim 3 wherein the plurality of gear teeth or recesses are in a helical pattern about a periphery of the middle core.

5. The spinal implant of claim 1 wherein the middle core is threadedly coupled to both the inner core and the outer core.

6. The spinal implant of claim 1 wherein the middle core has an outer periphery with a first thread and an inner periphery with a second thread, wherein the inner core includes an outer periphery with a third thread, and wherein the outer core includes an inner periphery with a fourth thread, wherein the first thread is one of the external threads of the middle core, the second thread is one of the internal threads of the middle core, the fourth thread is one of the internal threads of the outer core.

7. The spinal implant of claim 6 wherein the first thread and the second thread are different, wherein the first thread runs in a different direction than the second thread.

8. The spinal implant of claim 1 wherein the inner core includes a hollow interior portion and a threaded external portion, and a first end portion configured to engage a first vertebral body.

9. The spinal implant of claim 1 wherein the outer core includes a hollow threaded interior portion coaxially configured to receive the middle core and the inner core therein, and a second end portion configured to engage a second vertebral body.

10. The spinal implant of claim 9 wherein the middle core includes a hollow threaded portion coaxially configured to receive the inner core therein and a threaded external portion configured to engage the hollow interior portion of the outer core.

11. The spinal implant of claim 1 wherein the middle core includes a plurality of gear teeth or recesses cut into at least a portion of an outer periphery.

12. The spinal implant of claim 1 wherein the one or more locking mechanisms is configured to translate along the longitudinal axis.

13. The spinal implant of claim 1 wherein one or more locking mechanisms is a connecting sleeve locking the rotation about the longitudinal axis of the inner core with respect to the outer core.

14. The spinal implant of claim 1 wherein one or more locking mechanisms is a locking member and/or biasing member.

15. The spinal implant of claim 1 wherein at least one of a first end portion of the inner core and a second end portion of the outer core comprises a first attachment feature; one or more endplates coupled to the implant with the first attachment feature in at least one of the first end and the second end.

16. The spinal implant of claim 1 wherein a polyaxial endplate assembly is attached to at least one of the inner core and the outer core.

17. The spinal implant of claim 16 wherein the polyaxial endplate assembly is capable of pivoting along at least two intersecting axes disposed in the same plane which is not parallel to the longitudinal axis.

18. The spinal implant of claim 16 wherein the polyaxial endplate assembly includes a collar clamp and/or a locking member.

19. The spinal implant of claim 1 wherein a counterbore extends through an inner surface and an opposite outer surface of the outer core; a first set screw positioned in the counterbore to fix the inner core and/or middle core relative to the outer core.

20. The spinal implant of claim 1 further comprising a biased locking member to fix the rotation of the middle core and/or inner core relative to the outer core.

21. The spinal implant of claim 20 wherein the biased locking member includes one or more locking teeth and one or more biasing element.

22. The spinal implant of claim 1, wherein the one or more locking mechanisms coupled to the outer core are configured to:

lock a relative movement of the inner core with respect to the outer core through the engagement with the middle core and/or the inner core; and unlock the relative movement of the inner core with respect to the outer core through a disengagement with the middle core and/or the inner core.

23. A spinal implant comprising:

an expandable body having an adjustable length along a longitudinal axis thereof, the expandable body further comprising a first core, a second core configured to simultaneously translate and rotate within the first core along the longitudinal axis, and a third core configured to translate along the longitudinal axis within the second core, wherein rotation of the second core within the first core causes the third core to simultaneously translate along the longitudinal axis with respect to both the second core and the first core thereby adjusting a body length of the expandable body; and wherein:

one or more locking mechanisms coupled to the outer core are configured to physically contact and engage with the second core, the second core comprising external threads, the external threads comprising a plurality of gear teeth radially extended from the outer surface of the second core, and the one or more locking mechanism further comprising a locking member configured to move along the longitudinal axis to engage or disengage with one or more of the plurality of the gear teeth to lock or unlock second core relative to the first core.

24. The spinal implant of claim 23 further comprising a connecting sleeve, wherein the connecting sleeve prevents rotation of the third core relative to the first core.

25. The spinal implant of claim 23 wherein the second core includes the plurality of gear teeth and a plurality of recesses.

26. The spinal implant of claim 25 wherein the plurality of gear teeth or recesses are in a helical pattern about a periphery of the second core.

27. The spinal implant of claim 23 wherein the second core is threadedly coupled to both the third core and the first core.

28. The spinal implant of claim 23 wherein the second core has an outer periphery with a first thread and an inner periphery with a second thread, wherein the third core includes an outer periphery with a third thread, and wherein the first core includes an inner periphery with a fourth thread.

29. The spinal implant of claim 28 wherein the first thread and the second thread are different, wherein the first thread runs in a different direction than the second thread.

30. The spinal implant of claim 28 wherein the third core includes a hollow interior portion and a first end portion configured to engage a first vertebral body.

31. The spinal implant of claim 28 wherein the first core is configured to receive the second core therein, and the first core has a second end portion configured to engage a second vertebral body.

32. The spinal implant of claim 23 wherein the one or more locking mechanisms is configured to translate along the longitudinal axis.

33. The spinal implant of claim 23 wherein the one or more locking mechanisms is a connecting sleeve locking the rotation about the longitudinal axis of the third core with respect to the first core.

34. The spinal implant of claim 23 wherein the one or more locking mechanisms is a locking member and/or biasing member.

35. The spinal implant of claim 23 wherein at least one of a first end portion of the third core and a second end portion of the first core comprises a first attachment feature; one or more endplates coupled to the implant with the first attachment feature in at least one of the first end and the second end.

36. The spinal implant of claim 23 wherein a polyaxial endplate assembly is attached to at least one of the first core and the third core.

37. The spinal implant of claim 36 wherein the polyaxial endplate assembly is capable of pivoting along at least two intersecting axes disposed in the same plane which is not parallel to the longitudinal axis.

38. The spinal implant of claim 36 wherein the polyaxial endplate assembly includes a collar clamp and/or a locking member.

39. The spinal implant of claim 23 wherein a counterbore extends through an inner surface and an opposite outer surface of the first core and a first set screw is positioned in the counterbore to fix the third core and/or second core relative to the first core.

40. The spinal implant of claim 23 further comprising a biased locking member to fix the rotation of the second core and/or third core relative to the first core.

41. The spinal implant of claim 40 wherein the biased locking member includes one or more locking teeth and one or more biasing element.

42. The spinal implant of claim 23, wherein the one or more locking mechanisms coupled to the outer core are configured to:

lock a relative movement of the inner core with respect to the outer core through the engagement with the middle core and/or the inner core; and unlock the relative movement of the inner core with respect to the outer core through a disengagement with the middle core and/or the inner core.

\* \* \* \* \*